United States Patent
Cannon, Jr. et al.

(10) Patent No.: US 11,357,492 B2
(45) Date of Patent: Jun. 14, 2022

(54) LAPAROSCOPIC INTRAABDOMINAL WORK TABLE RETRACTOR, INSTRUMENT AND POSITIONER

(71) Applicants: Charles Cannon, Jr., Jersey Shore, PA (US); Elan Salzhauer, Skaneateles, NY (US)

(72) Inventors: Charles Cannon, Jr., Jersey Shore, PA (US); Elan Salzhauer, Skaneateles, NY (US)

( * ) Notice: Subject to any disclaimer, the term of this patent is extended or adjusted under 35 U.S.C. 154(b) by 0 days.

(21) Appl. No.: 16/416,407

(22) Filed: May 20, 2019

(65) Prior Publication Data
US 2020/0367877 A1 Nov. 26, 2020

(51) Int. Cl.
*A61B 17/02* (2006.01)
*A61B 17/34* (2006.01)
(Continued)

(52) U.S. Cl.
CPC ...... *A61B 17/0281* (2013.01); *A61B 17/3417* (2013.01); *A61B 34/70* (2016.02);
(Continued)

(58) Field of Classification Search
CPC . A61B 17/0281; A61B 17/3417; A61B 17/02; A61B 17/3423; A61B 1/008; A61B 1/0016; A61B 1/0052; A61B 1/00128; A61B 1/045; A61B 1/051; A61B 2034/301; A61B 2034/742; A61B 90/37;
(Continued)

(56) References Cited

U.S. PATENT DOCUMENTS

2011/0276083 A1* 11/2011 Shelton, IV ........... A61B 17/29
606/205
2013/0281924 A1* 10/2013 Shellenberger .. A61B 17/00234
604/95.01
(Continued)

OTHER PUBLICATIONS

First Human Experience Using the Dynamic Laparoscopic Novatract(TM) Retractor by Koji Park, MD et al.,Society of American Gastrointestinal and Endoscopic Surgeons 2014, meeting, abstract at: https://www.sages.org/meetings/annual-meeting/abstracts-archive/first-human-experience-using-the-dynamic-laparoscopic-novatracttm-retractor/; and animation at https://www.youtube.com/watch?v=ZoWAR52y58U.
(Continued)

*Primary Examiner* — Pedro Philogene
(74) *Attorney, Agent, or Firm* — Ohlandt, Greeley, Ruggiero & Perle, L.L.P.

(57) ABSTRACT

A SURGICAL ACCESSORY TO BE USED WITHIN THE BODY WHICH IS ATTACHED TO THE ABDOMINAL WALL, FOR HOLDING AND POSITIONING TISSUE AND SURGICAL IMPLEMENTS DURING LAPEROSCOPIC OR ROBOTIC SURGERY.
THIS CONSIST OF A COLLAPSABLE TABLE WITH ATTACHED FLEXABLE OR FIXED ARMS WITH ACCESSORIES FOR HOLDING SURGICAL TOOLS OR MANIPULATING TISSUES OR ORGANS.
A SURGICAL CLIP THAT ATTACHES TO OTHER INSTRUMENTS OFFERING MULTIPLE APPLICATIONS FOR CAPTURING AND SECURING OTHER ACCESSORIES SUCH AS CAMERAS OR INTRA OPERATIVE ULTRASOUND PROBES.

32 Claims, 66 Drawing Sheets

(51) Int. Cl.
*A61B 34/00* (2016.01)
*A61B 17/072* (2006.01)
*A61B 17/04* (2006.01)
*A61B 17/00* (2006.01)

(52) U.S. Cl.
CPC .............. *A61B 2017/00637* (2013.01); *A61B 2017/0464* (2013.01); *A61B 2017/07257* (2013.01); *A61B 2017/3411* (2013.01)

(58) Field of Classification Search
CPC ............. A61B 90/11; A61B 90/361; A61B 2017/07257; A61B 2017/3411; A61B 2017/0464; A61B 2017/00637; A61B 2017/00101; A61B 2017/00199; A61B 2017/00309; A61B 2017/00314; A61B 2017/00327; A61B 2017/00473; A61B 2017/2906; A61B 2017/347; A61B 34/70; A61B 34/76; A61B 34/77; A61B 34/30; A61B 34/34; A61B 2090/506; A61B 2090/571; A61B 18/1206; A61B 18/1482; A61B 2018/00178; A61B 2018/00595; A61B 2018/1253
See application file for complete search history.

(56) References Cited

U.S. PATENT DOCUMENTS

| | | | |
|---|---|---|---|
| 2014/0005640 A1* | 1/2014 | Shelton, IV | A61B 34/71 606/1 |
| 2014/0148806 A1* | 5/2014 | Witt | A61B 18/1485 606/45 |
| 2016/0022313 A1* | 1/2016 | Yoshida | A61B 17/3478 606/185 |

OTHER PUBLICATIONS

How We Made an Octopus-Inspired Surgical Robot Using Coffee, Kasper Althoefer, The Conversation, May 20, 2015, and embedded videos at: https://www.scientificamerican,com/article/how-we-made-an-octopus-inspired-surgical-robot-using-coffee/.

* cited by examiner

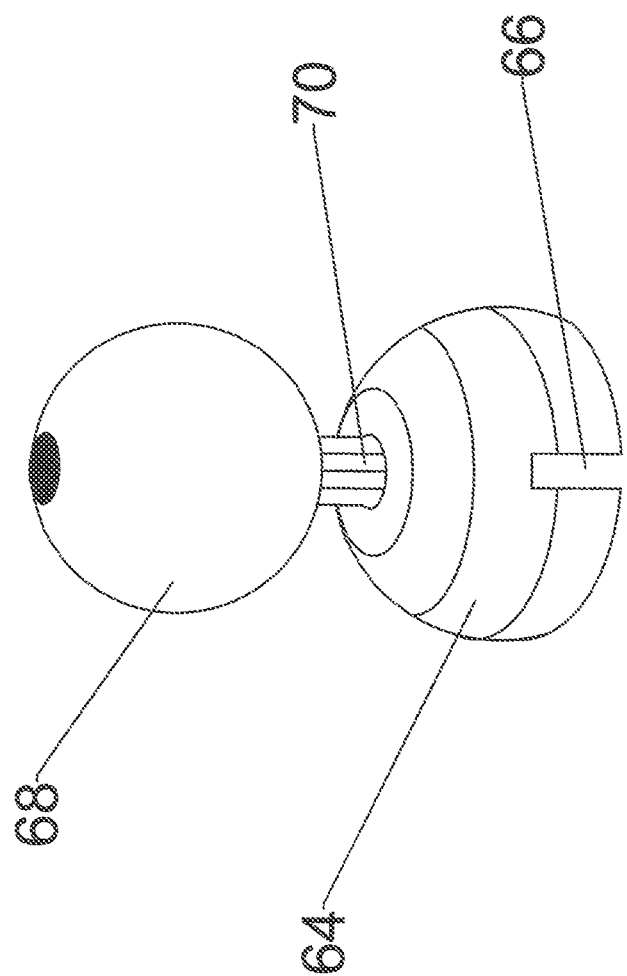

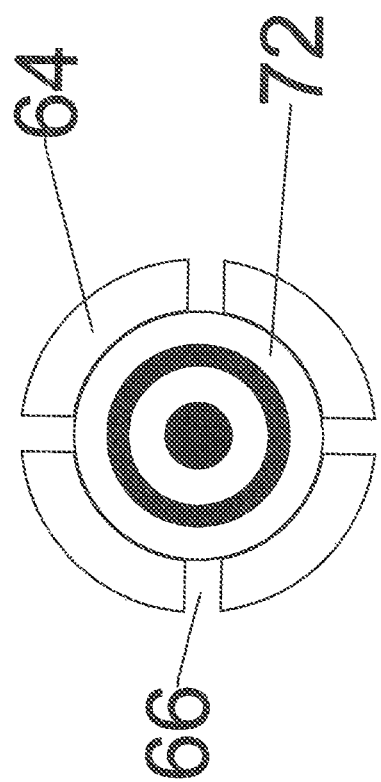

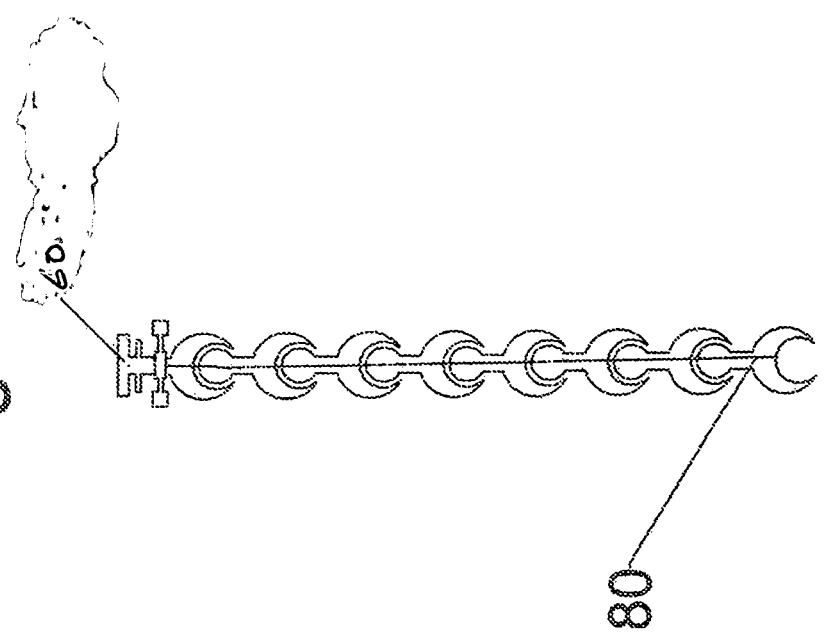

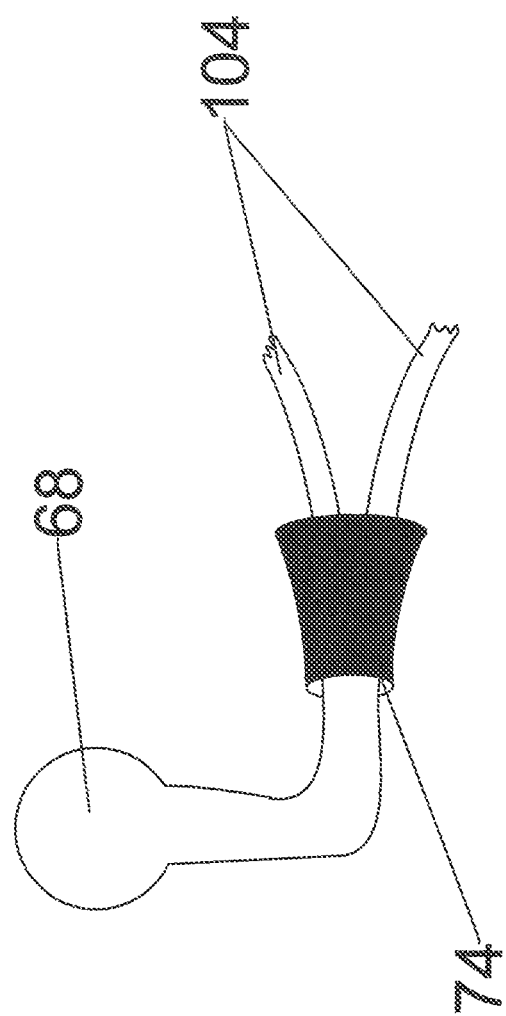

Figure 31B
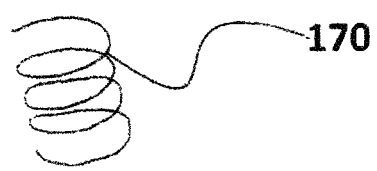
170
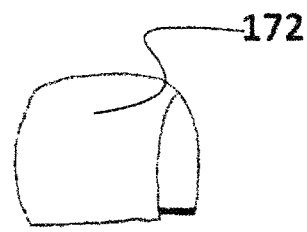
172
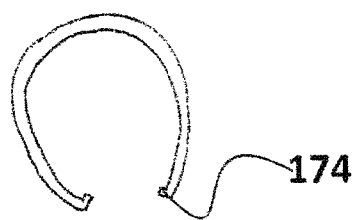
174

Figure 31C
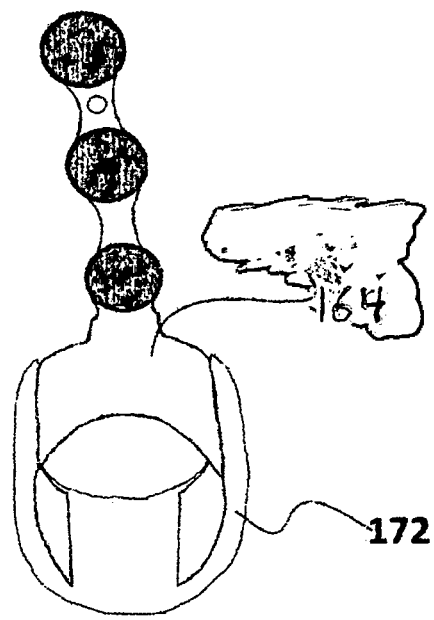
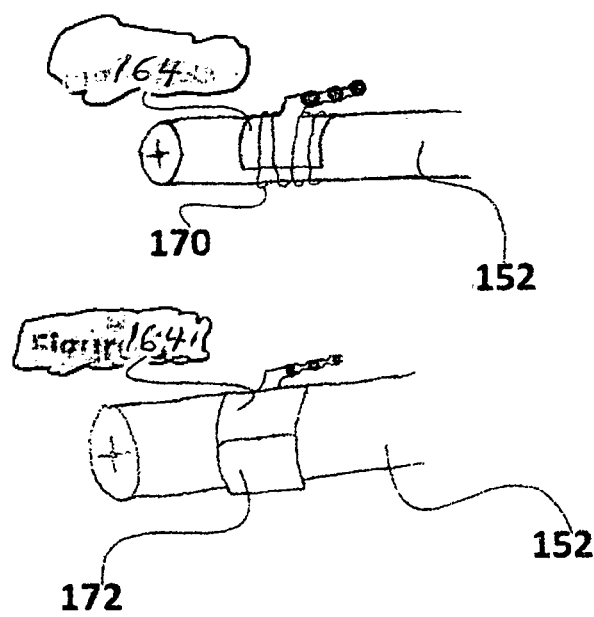

LAPAROSCOPIC INTRAABDOMINAL WORK TABLE RETRACTOR, INSTRUMENT AND POSITIONER

This patent application claims priority from and the benefit of provisional patent application Ser. No. 62/674,063 filed on May 21, 2018, which is incorporated herein by reference for all purposes.

FIELD OF THE DISCLOSURE

This application relates to surgical devices that can be inserted through a laparoscopic trocar or open incision and fastened inside the body to move, hold, retract and position tissues, organs and/or instruments in order to enhance a surgeon's ability to perform an operation.

BACKGROUND ART

Advances in surgical procedures are shifting to smaller incisions resulting in quicker recoveries with better post-operative results. The most recent technology genre which has emerged is laparoscopic and robotic surgery, where small access holes called ports are placed through the abdominal cavity and instruments are inserted through these ports to perform surgery. These procedures are performed under visual observation using small cameras.

Currently, laparoscopic retracting and positioning devices are controlled by the surgeon and/or assistant through working ports. These devices are quite useful yet they share several important limitations. They monopolize a port. They are limited by their inherent lack of flexibility which is dictated by a straight line trajectory starting at the port and ending at the organ or tissue structure. Finally, they often obstruct the surgeons operating view or compete for intra-abdominal space with other surgical instruments. All of these limitations can potentially complicate or lengthen a surgical procedure.

SUMMARY OF THE DISCLOSURE

To address the abovementioned limitations, we propose a novel device that will position and retract organs and tissues during surgery without tying up a laparoscopic trocar. It will not interfere or compete for space in the limited intra-abdominal cavity. The device will be secured to the intra-abdominal wall by a suture passed though the abdominal wall to an exterior stabilizing device. The device does not require a dedicated port. It requires no dedicated skin incisions as the intra-abdominal components can be passed into the abdominal cavity through existing ports. The device has grasping, retracting, imaging and visual capabilities. The device has the potential to reduce surgery time, reduce skin incisions and port usage, improve surgical visibility, allow for ultrasound imaging or novel camera angles for better visibility, improve the intra-operative conditions to perform a procedure, allow easier surgical access to difficult locations in surgery.

The device can also be used in open surgery. Benefits include retraction and stabilization from an area outside of the main retractor. This can benefit the surgeon by decreasing the attachments to the main retractor thereby increasing the space available for the surgeon and assistant to complete a given surgery. In addition, the novel angel of retraction away from the main open incision offers the surgeon increased flexibility for retraction or stabilization of organ structures.

The anvil handle medical probe consists of a straight graspable anvil along with one or two trailer balls on either end. The instrument is best suited for laparoscopic and robotic surgery but can be used in other applications. It offers more flexibility and control for physicians when trying to manipulate laparoscopic tools. The anvil handle allows the laparoscopic instruments or the tentacles of the Surgical Octopus to grasp items in multiple ways i.e. from one side, from both sides, or from the top, front or rear. It can be attached to numerous medical devices such as ablative devices, intra-operative ultrasound imaging probes, remote cameras, or internal positioning devices. The handle may be customized to fit existing devices.

The anvil handle (anvil) allows a medical device such as an intra-operative drop in ultrasound probe or camera to be grasped quickly and securely from any direction to better complete a surgical task. In addition, the anvil allows for additional accessory handles to be used in other applications.

OBJECTIVES

Objective number one is to provide an intraoperative base plate with movable adjustable arms to hold and position tissues, organs and/or instruments According to an embodiment, a device is provided which can be passed through a 10 mm or 12 mm trocar and assembled by the surgeon inside the cavity of the body during surgery.

The device is secured to the abdominal wall and is used to retract organs and tissues to allow the surgeon better visibility and accessibility during a surgical procedure.

The device is comprised of several parts depending on the needs of the surgeon. The device can be anchored or free-floating dependent on the type of operation.

The device consists of a base plate, anchoring system and one or more articulating arms which can be positioned and anchored to a desired configuration.

In addition, the articulating arms can accommodate various devices to hold and manipulate tissues or instruments.

An accessory channel allows for vacuum or pressure to inflate expansion devices or suction to attach the articulating device to specified tissue. Additional embodiments include signal or low power energy to operate other devices such as intraoperative cameras.

The anchoring system is passed through an accessory port and once expanded is attached to the abdominal wall with a suture or other method, in a location by using physician preferences.

The positioning arms or accessories are then passed through a port and attached to the base anchor. They are then manipulated using laparoscopic or robotic instruments during laparoscopic surgery, or via direct manipulation during an open procedure. Once in place a locking device is activated, and the arms will remain locked until the physician releases the locks.

The arms can be easily relocated or repositioned by simply releasing the locks, repositioning the arms and then relocking During surgery additional devices can be passed through ports and attached to other areas of the anchoring system as needed.

Instrument clips with the Anvil attachment can be used to secure devices such as ultrasounds or cameras or other laparoscopic devices Objective number two of this invention is to provide an attachment that can be used on laparoscopic equipment and surgical tools that allows for quick and easy attachment and detachment of surgical implements and can be incorporated in a fixed design on diagnostic equipment or therapeutic devices. or incorporated in a clip attachment.

This quick connect device further adds to the ease of operation with both anvil and ball (or all three) as optional attachments to a probe. This allows for easier manipulation of intra-abdominal surgical devices and tools. The addition of an optional "trailer ball" offers the physician the option to move a probe and device and/or apply pressure to the device in off plane axes using two laparoscopic instruments Objective number three of this invention is to allow doctors performing intra-abdominal robotic surgery to complete surgeries quicker by allowing them to quickly grip and move surgical tools more easily.

The removable clip attachment with anvil attached permit accessories to be grasped in multiple positions. The anvil handle offers numerous ways to grasp the medical device quickly and securely.

Accessory Handles can be quickly attached allowing for a quick transition from the laparoscopic table, to robot or laparoscopic control to an open procedure quickly, as needed.

BRIEF DESCRIPTION OF THE DRAWINGS

FIG. 5B illustrates a connecting ball and socket of the accessory arm of FIG. 5.
FIG. 5C is cross-section of the socket of FIG. 5B.
FIG. 6A illustrates an embodiment of the arm of FIG. 6 with a connecting ball and socket.

FIG. 11 illustrates a tissue spreader device for holding open incisions.

FIG. 31B illustrates safety elements to secure the clip.

FIG. 31C illustrates the safety elements of FIG. 31B in place.

DETAILED DESCRIPTION OF THE PREFERRED EMBODIMENTS

Figure 1:
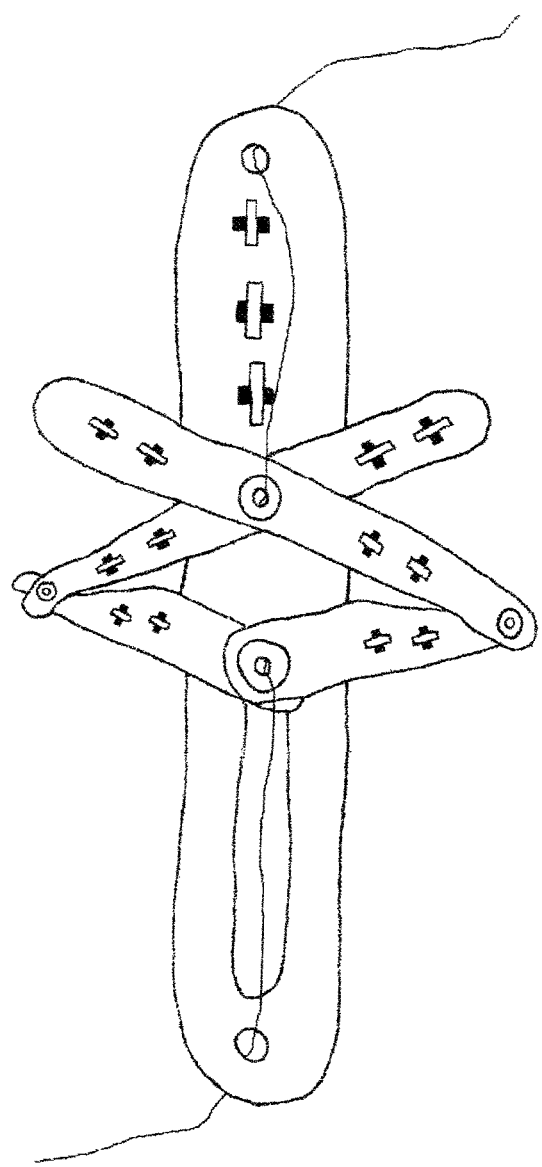
FIG. 1 illustrates a laparoscopic table.

FIG. 1 1 embodies an overall depiction of the laparoscopic table.

Figure 1A:
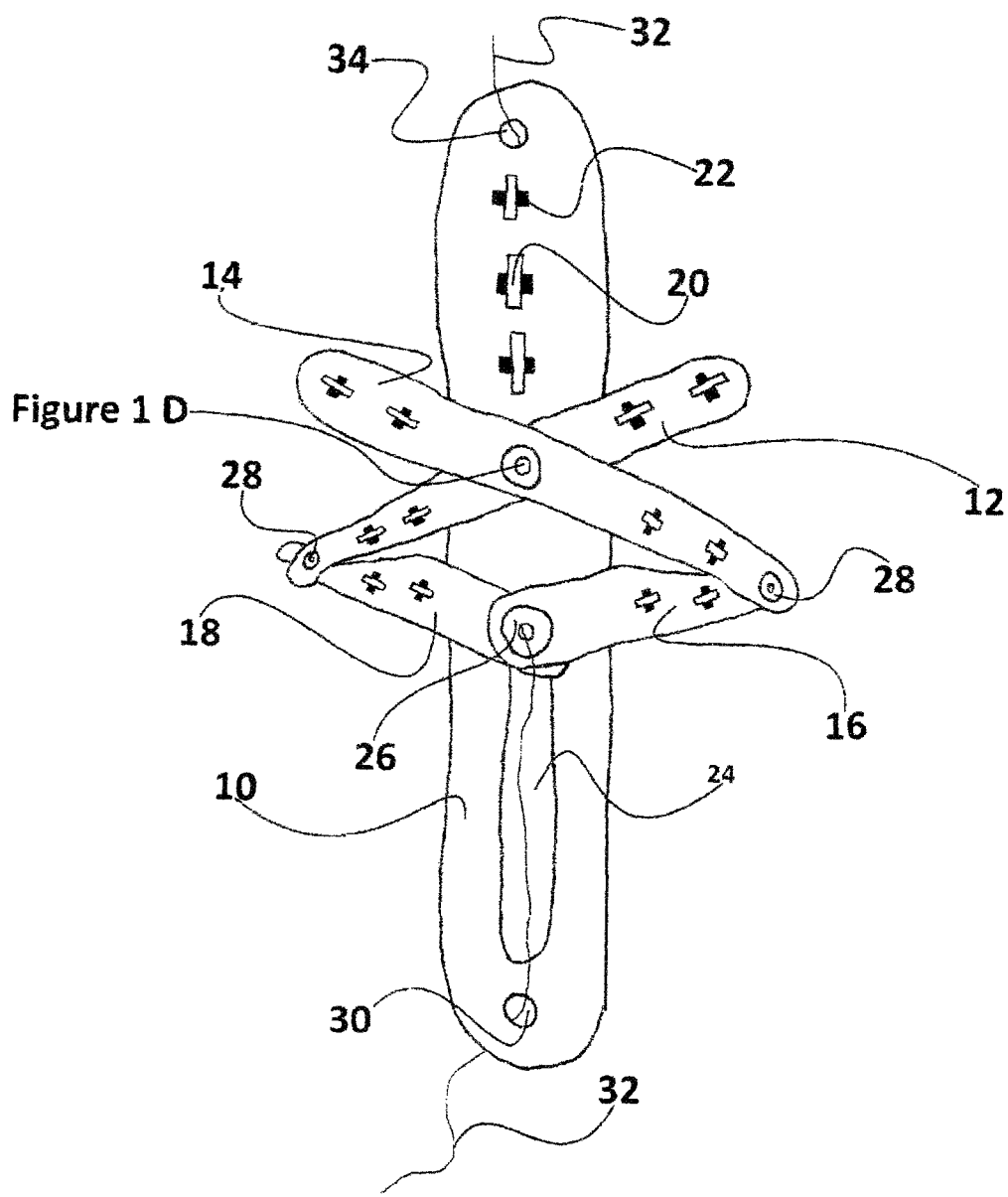
FIG. 1A illustrates the laparoscopic table of FIG. 1, expanded
Figure 1B:
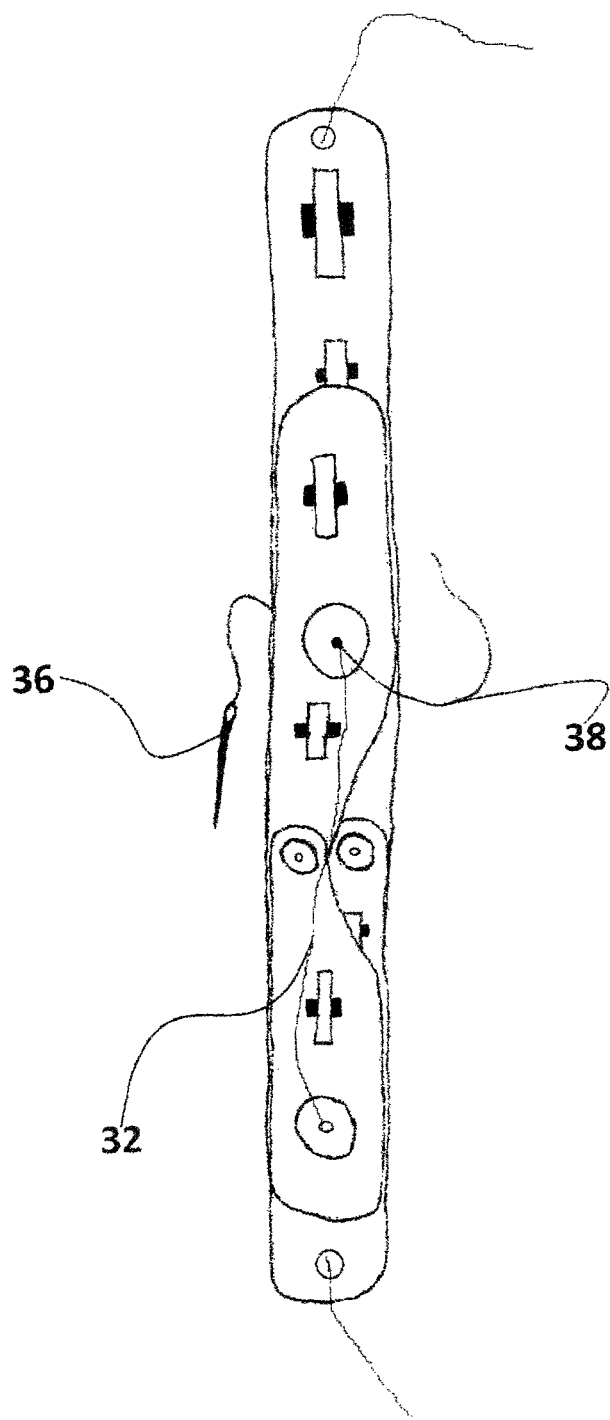
FIG. 1B illustrates the laparoscopic table of FIG. 1A collapsed for insertion.

FIG. 1A is a detailed drawing of the expanded table. FIG. 1B embodies the table collapsed for insertion. The main components embody one main plate (FIG. 1A (10)) with two stabilizer wings (FIG. 1 (right wing (12) and left wing (14)). The wings are deployed by the auxiliary stabilizer actuator wings (FIG. 1A right (16) and left (18)). Grommet (FIG. 1D) is a pivot point and the main hinge of the unit. This allows the wings to pivot, as well as, provides a suture central securing point and auxiliary channel (FIG. 1D (42)) after insertion. The deployment cord (FIG. 1A (32)) is pulled until grommet (FIG. 1A (26)) is pushed forward in slot (FIG. 1A (60)) until stabilizer wings are fully extended and grommet (FIG. 1A (26)) reaches the opposite end in slot (FIG. 1A (24)). This controls the extent of deployment.

Figure 1C:
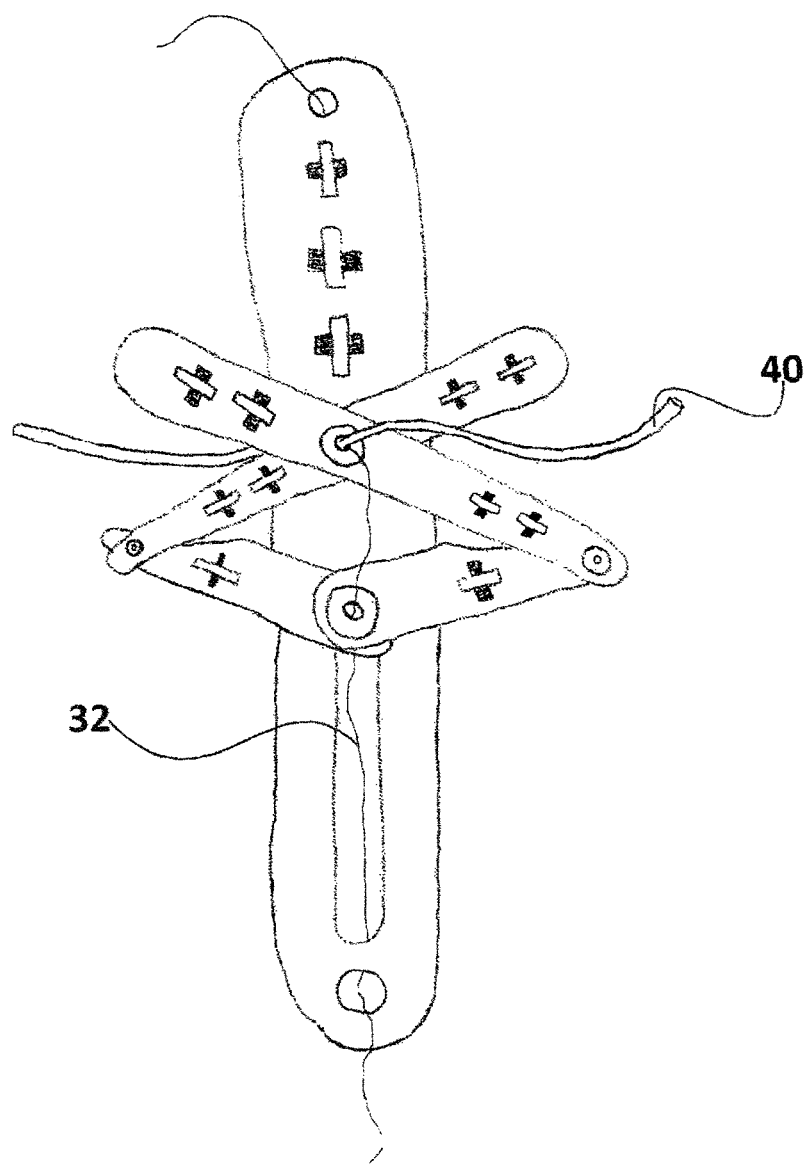
FIG. 1C illustrates the laparoscopic table of FIG. 1, in use.
Figure 1D:
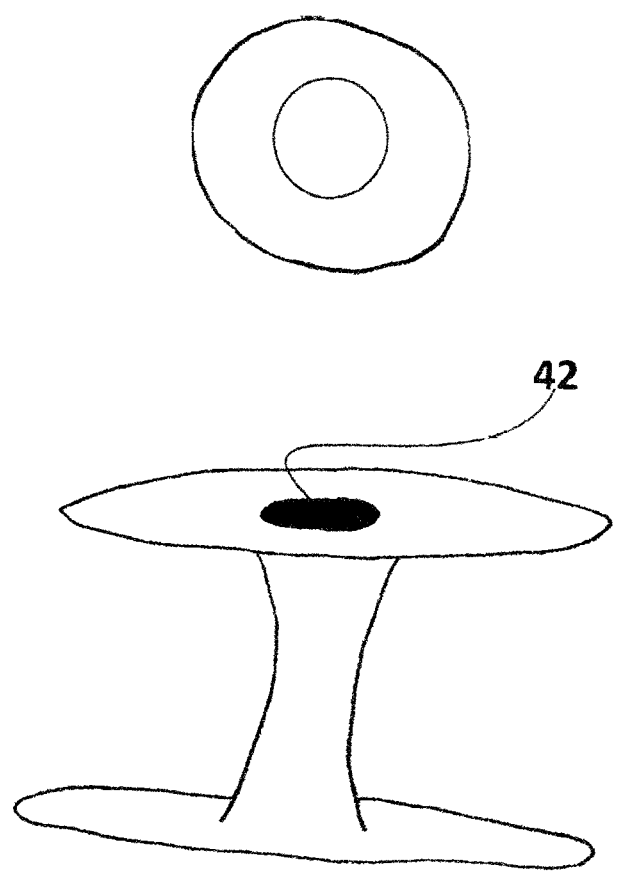
FIG. 1D illustrates a pivot point and the main hinge of the laparoscopic table of FIGS. 1A, 1B and 1C.
Figure 32:
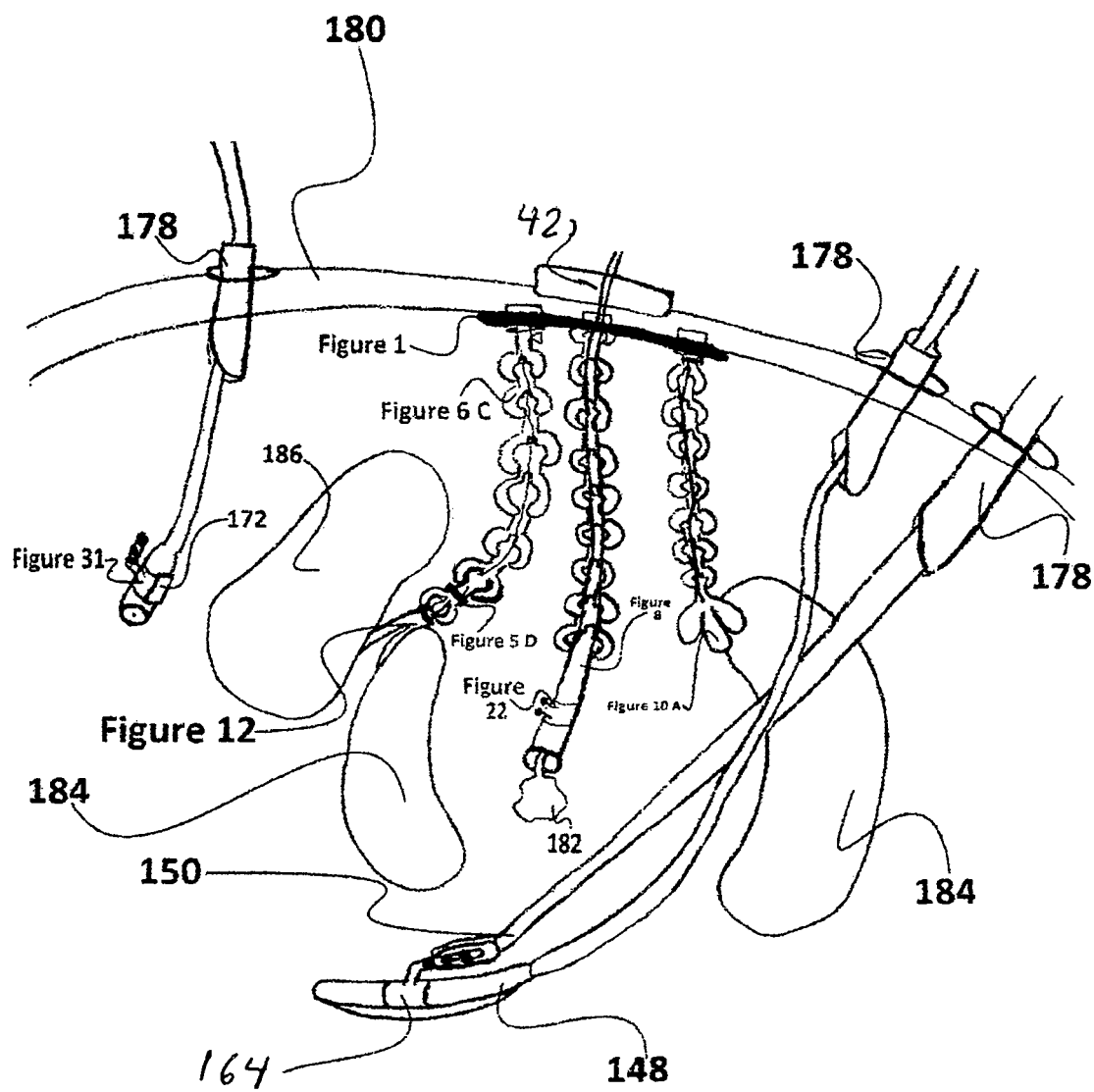
FIG. 32 illustrates the devices used in a procedure.

A Keith needle, or other type needle (FIG. 1B (36)) with suture (FIG. 1B (38)), which can be attached to the device or passed in separately, is removed from the device and passed through the abdominal wall (FIG. 32 (180)) through the grommet (FIG. 1D). The suture (FIG. 1B 38) is attached to and secured outside the abdominal wall to a tensioning device (FIG. 4 (58)). Additional anchor points can be secured in the same manner through grommet (FIG. 1A (26)). Another alternative fastening method is to pass a needle from the outside abdominal wall through the grommet (FIG. 4) and then secured with a clip or other desired surgical devices. Once in place the base place is cinched down for stability. A backing plate constructed of soft material (FIG. 3) can be added to protect the surfaces from abrasions.

Once in place the table (FIG. 1) is ready to accept the desired accessory arms.

FIG. 1B embodies the table collapsed FIG. 1C embodies the laparoscopic table with a suction tube passed through the main grommet (FIG. 1D).

Figure 2:
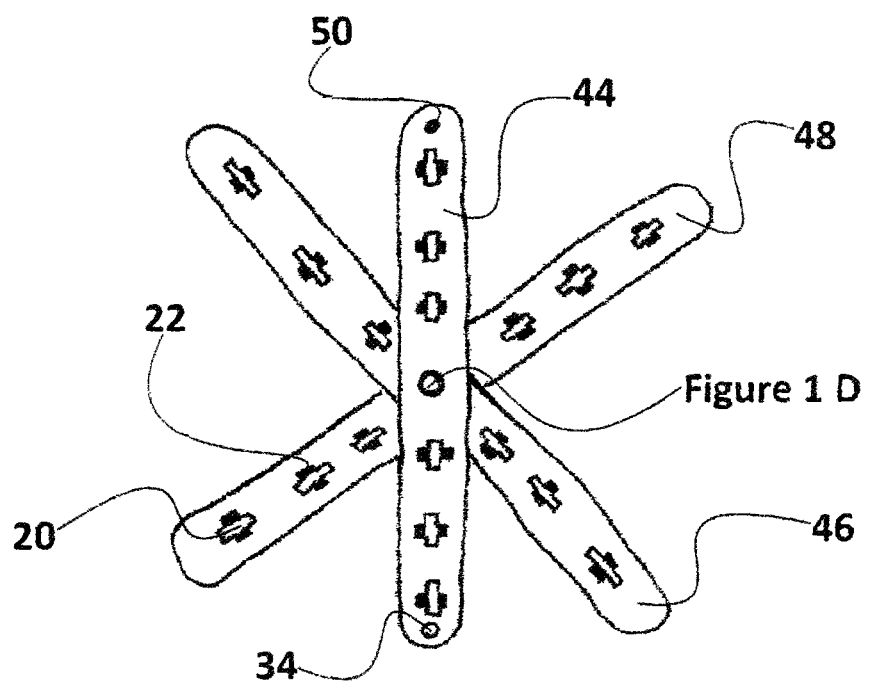
FIGS. 2A and 2B illustrate a smaller version of the table used to clamp and secure surgical instruments or equipment requiring external signals.

FIG. 2 embodies a smaller version of the table used to clamp and secure surgical instruments or equipment requiring external signals. This table is deployed by pulling left on the front ball (FIG. 2 (50)) and right on the back ball (FIG. 2A (50)). Grommet (FIG. 1D) is used in the same manner as FIG. 1.

Figure 2A:
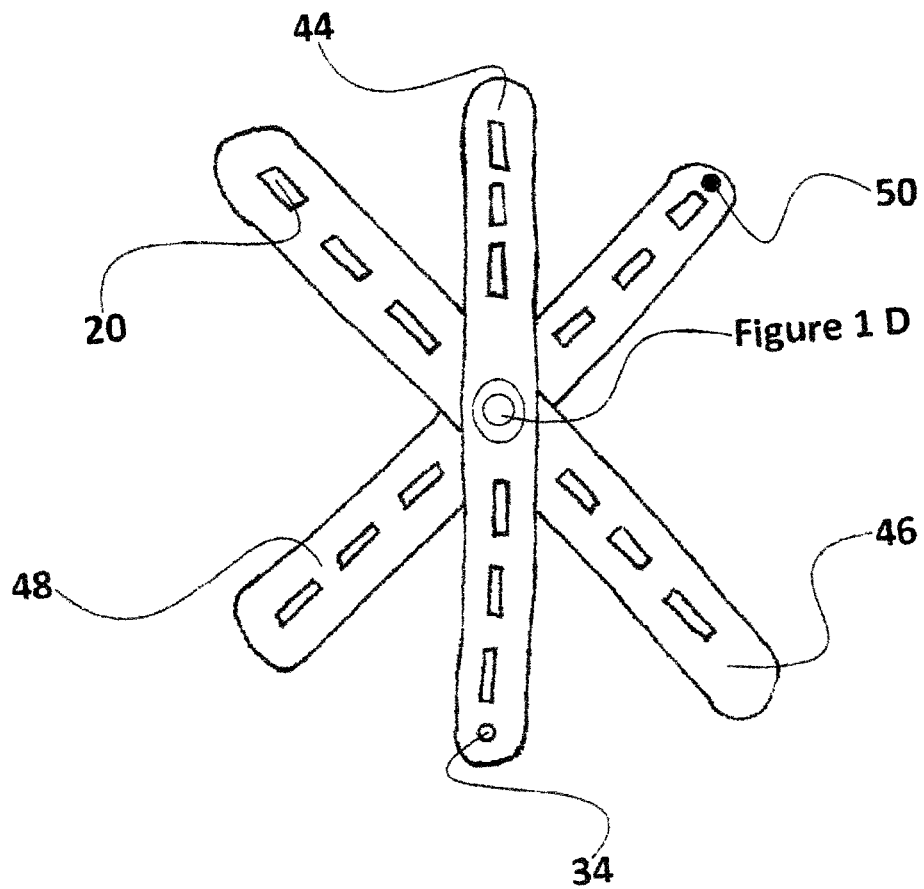

FIG. 2A is the view of the back of FIG. 2

Figure 3:
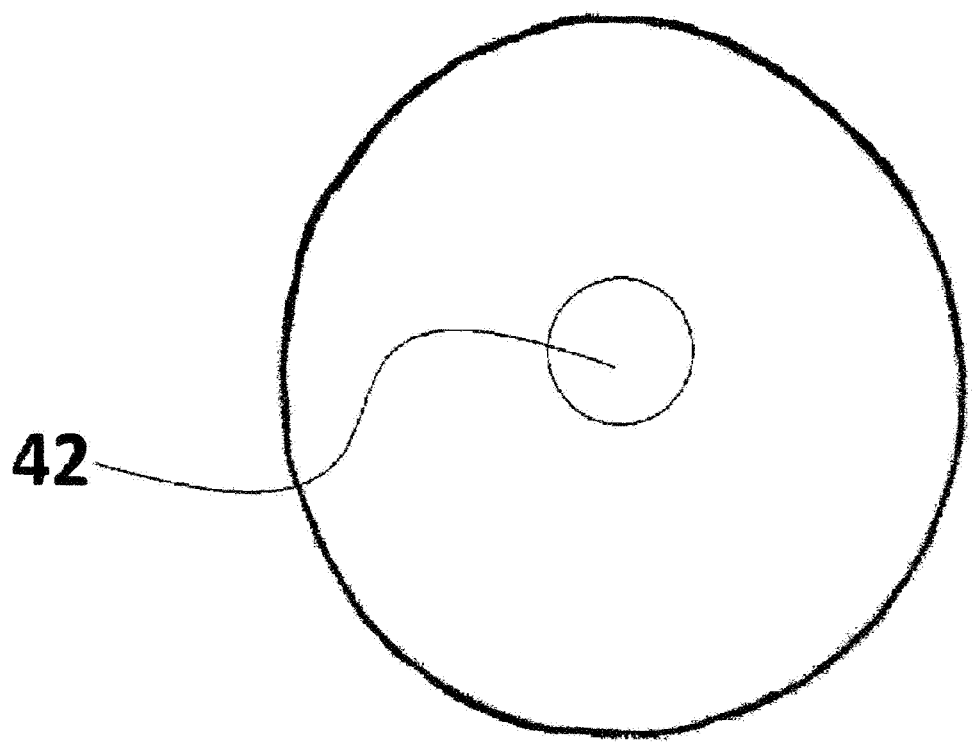
FIG. 3 illustrates a protecting foam.

FIG. 3 embodies a cushion to protect the abdominal wall from tissue abrasions while the table is secured.

Figure 4:
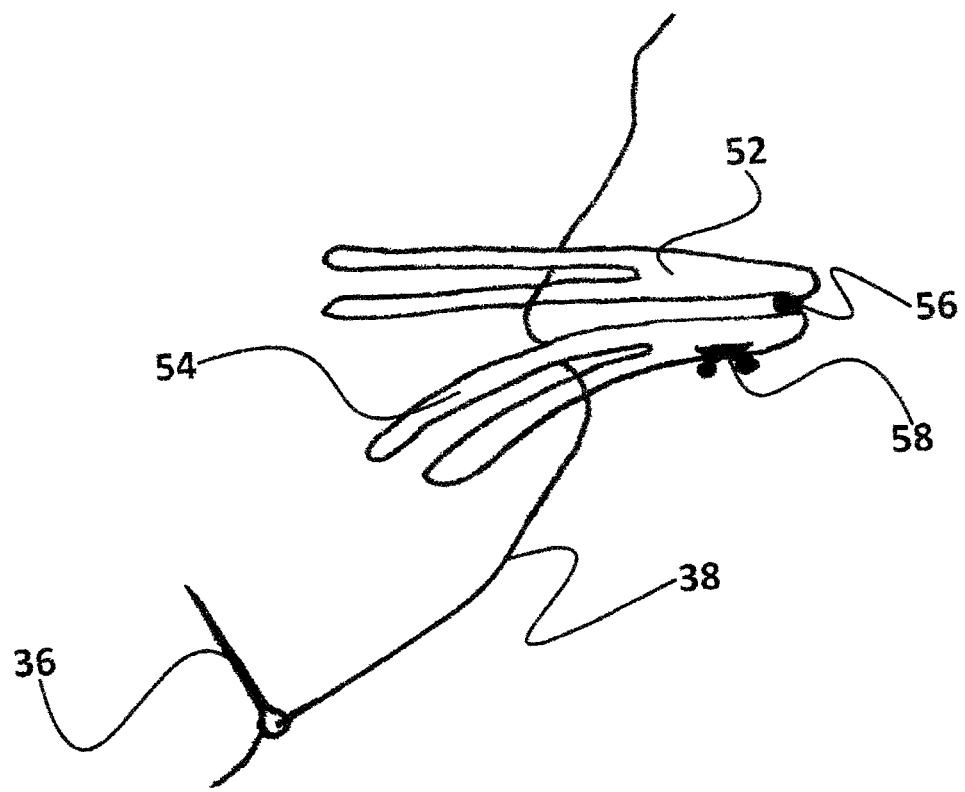
FIG. 4 illustrates a tensioning device inserted to provide tension on the cable or suture.
Figure 5:
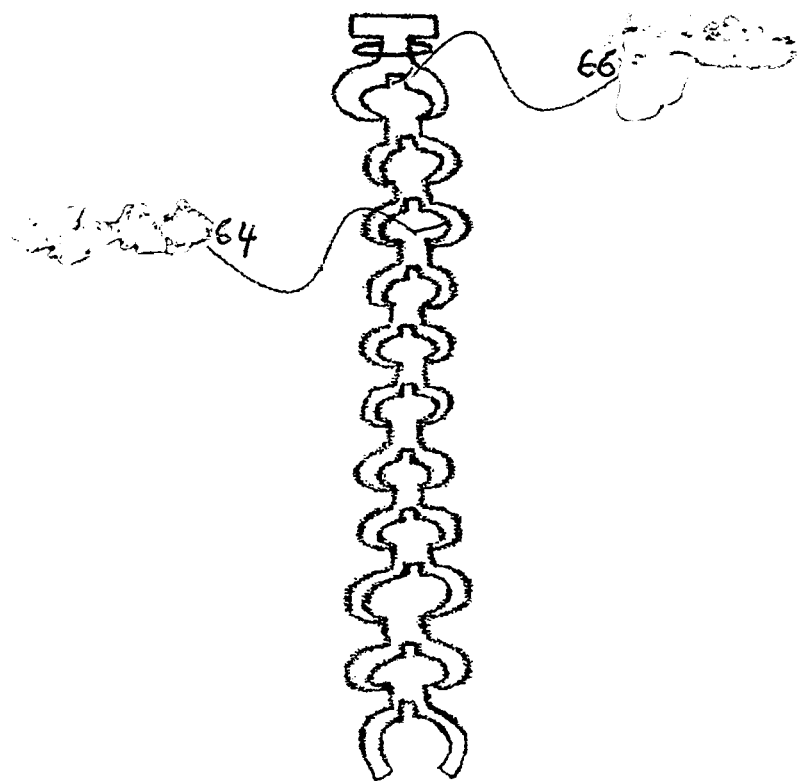
FIG. 5 illustrates an accessory arm.

FIG. 4 is a tensioning device inserted to provide tension on the cable or suture to hold the table in place and provides the correct tension to avoid over tension. The spring tensioner is compressed where top (FIG. 4 (52)) is against the protecting foam (FIG. 3). The suture is placed in the fork of the upper and lower springs and secured to the anvil (FIG. 4 (58)). The tension is then released from the spring allowing the proper tension to be applied to the laparoscopic table to hold secure FIG. 5 is the accessory arm consisting of multiple ball and socket knuckles or other flexible malleable material. In the embodiment of ball and socket configuration, the first joint consists of a top locking connector, also referred to as a T-Lock (FIG. 5A), and a connecting ball (FIG. 5B). In the embodiment of the octopus arm configuration, the T of the connector (FIG. 5A (60)) lifts into the slot (FIG. 1A (20)), then turning the T lock 90 degrees to lock the arm into place (FIG. 1A (22)). The semi-soft circular foam (FIG. 5A (62)); also known as the foam stabilizer; located under the locking t top (FIG. 5A (60)) helps keep the octopus arm rigid. A connector ball (FIG. 5B (68)) is then attached to the socket (FIG. 5A (64)) at the bottom of the t lock by inserting the ball into the socket. A. high friction compound (FIG. 5C (72)) is coated on the inside of each socket to ensure rigidity in the arm. Slots are located on the socket (FIG. 5B (66)) for locking cords to travel up and down the arm locking the arm into the desired position. Each successive ball joint consists of a ball (FIG. 5B (68)) and socket (FIG. 5B (64)), either preassembled or assembled to fit the desired length. The first joint may consist of one of the various steerable or non-steerable top locking connectors. Other methods of attachment to the table may include quick connect magnets (FIG. 5H (190)) or other mechanical attachments.

One embodiment is a ball and socket configuration (FIG. 5) consisting of several ball (FIG. 5B (68)) and socket (FIG. 5B (64)) joints or connections. This is referred to as an octopus arm.

Figure 5A:
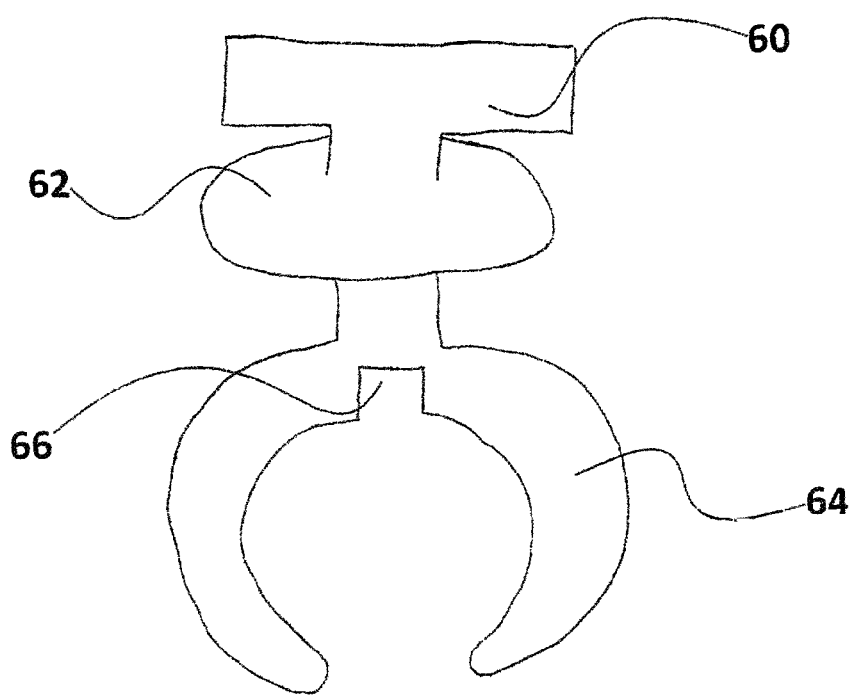
FIG. 5A illustrates a T-Lock of the accessory arm of FIG. 5.

A locking connector with ball (FIG. 5D) is then added to the arm (FIG. 5F) for holding an accessory or other desired object. The ball (FIG. 5D (68)) is inserted into the last socket of the arm. The locking connector has 3 grasping legs (FIG. 5D (78)) with the high friction compound (FIG. 5D (72)) on the inside to grab the ball of an accessory and assist keeping it in the desired position. The collar (FIG. 5D (74)) is cinched down to activate the legs to close. The collar is held in placed by threads (FIG. 5D (76)) to ensure jaws do not open. An octopus arm may also be made up of the locking connectors (FIG. 5E).

Figure 5D:
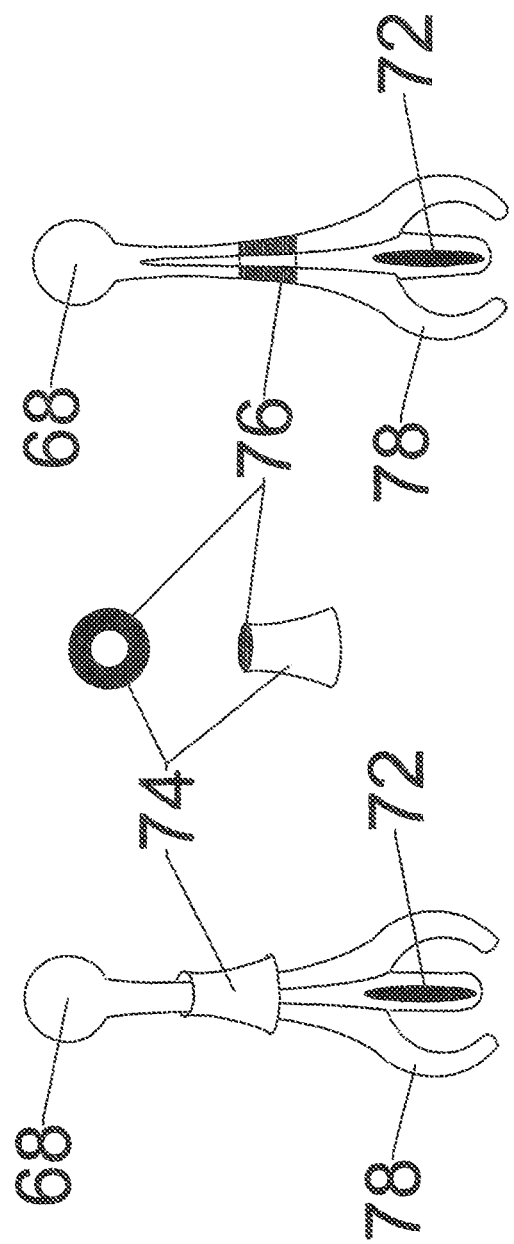
FIG. 5D illustrates a connector for addition to the accessory arm of FIG. 5.
Figure 5E:
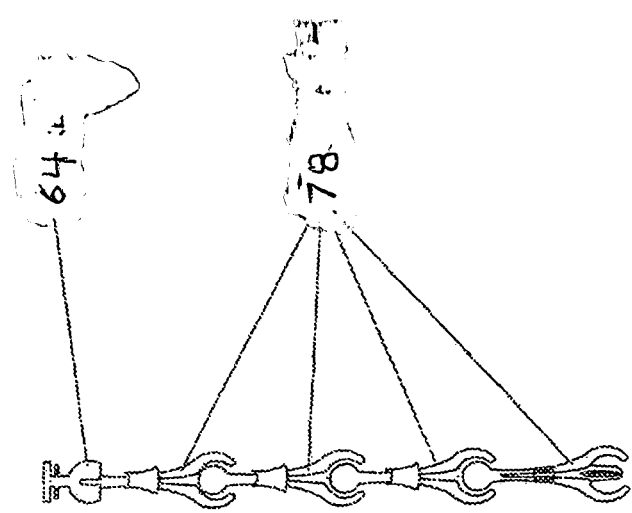
FIG. 5E illustrates an octopus arm made up of the locking connectors.
Figure 5F:
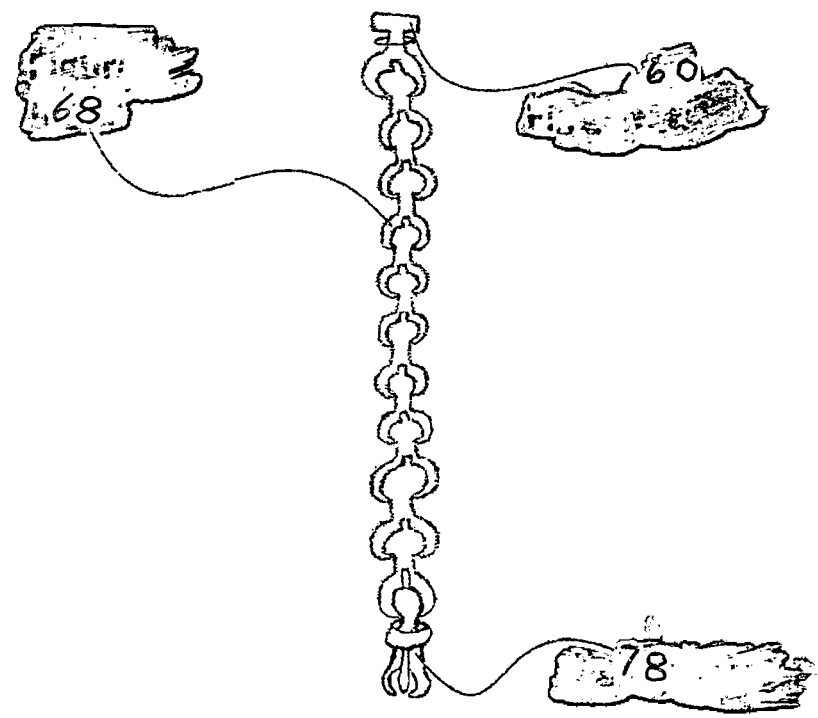
FIG. 5F illustrates a locking connector with ball added to an accessory arm.
Figure 5G:
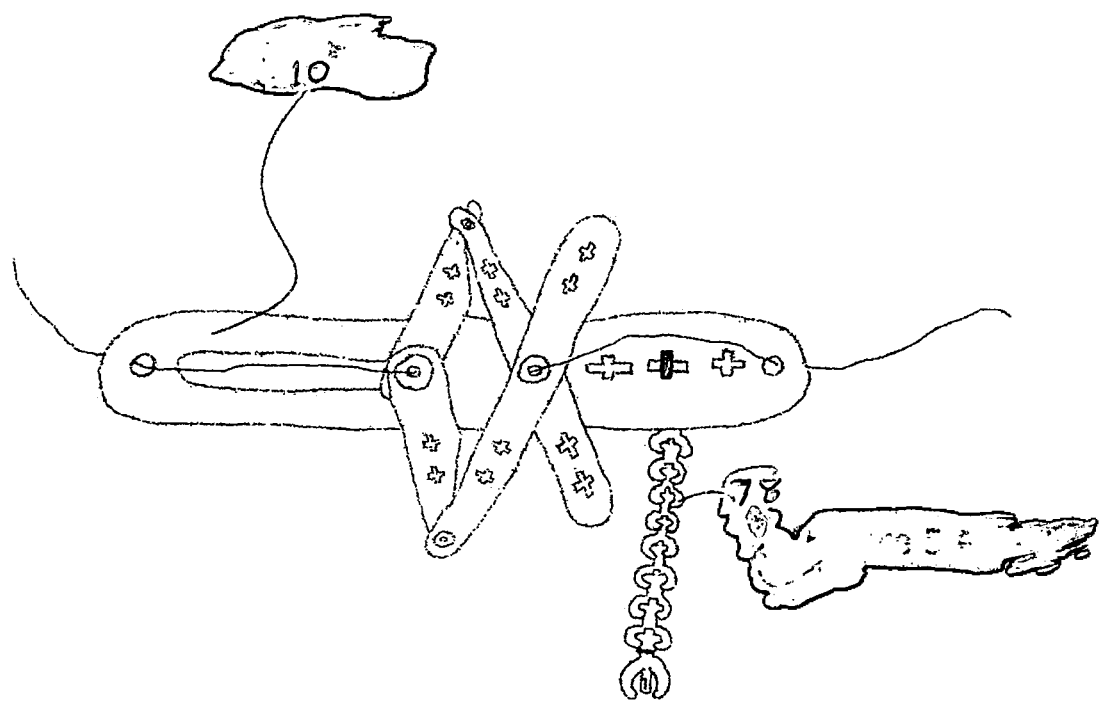
FIG. 5G illustrates the assembly of an accessory arm to the table of FIG. 1.

FIG. 5G depicts the complete assembly of the arm (FIG. 5F) to the table (FIG. 1).

A magnet connector with socket (FIG. 5H) may be used in place of the T-lock (FIG. 5A) to connect the arm to the table for quickly switching arms.

Figure 6:
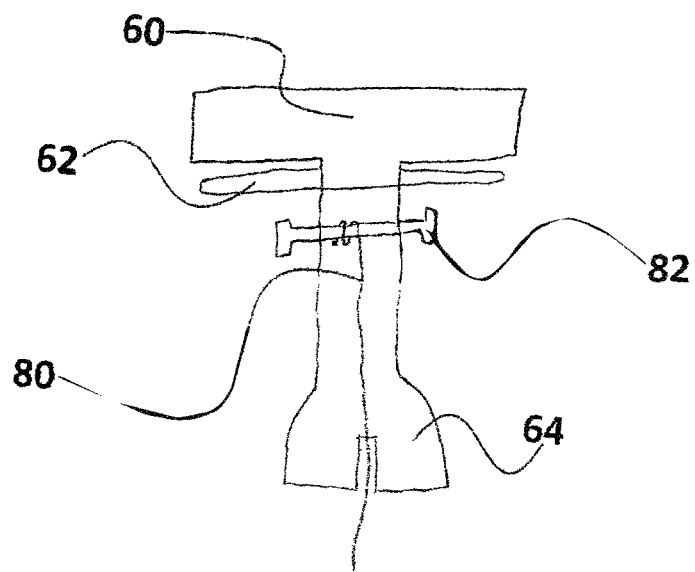
FIG. 6 illustrates another configuration of an octopus arm.

Another configuration of an octopus arm is made similar to the one described above but manipulated by cords running the length of the arm (FIG. 6A). The arm consists of a similar T-lock with an additional cord tensioner added below the foam stabilizer on t lock, and the connector balls. When turning the cord tensioner handle (FIG. 6 (82)), it will manipulate the cord (FIG. 6 (80)) and in turn control the movement of the arm. The tensioning cord is tightened or steered through the control line or lines. using various methods: such as a screw (FIG. 6B and FIG. 6C), A nut on threads embodied in FIG. 6D, Other method of applying tension to the locking cord or cords may be used.

Other methods of tightening may be incorporated as the cable (FIG. 6A (80)) is tightened the octopus arm becomes ridged.

Figure 5H:
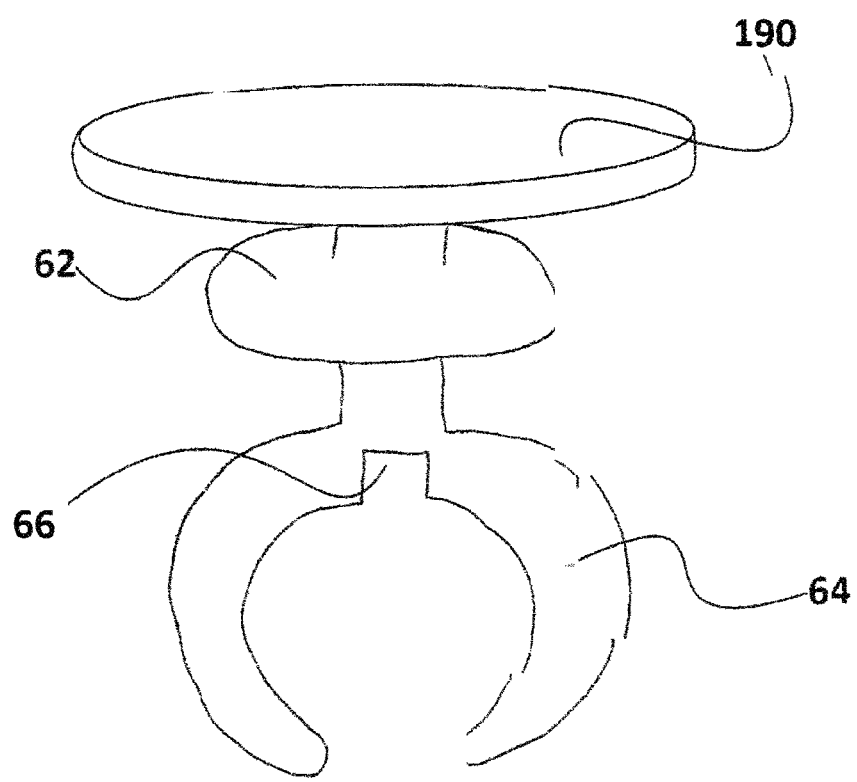
FIG. 5H illustrates a magnet connector with a socket.
Figure 5J:
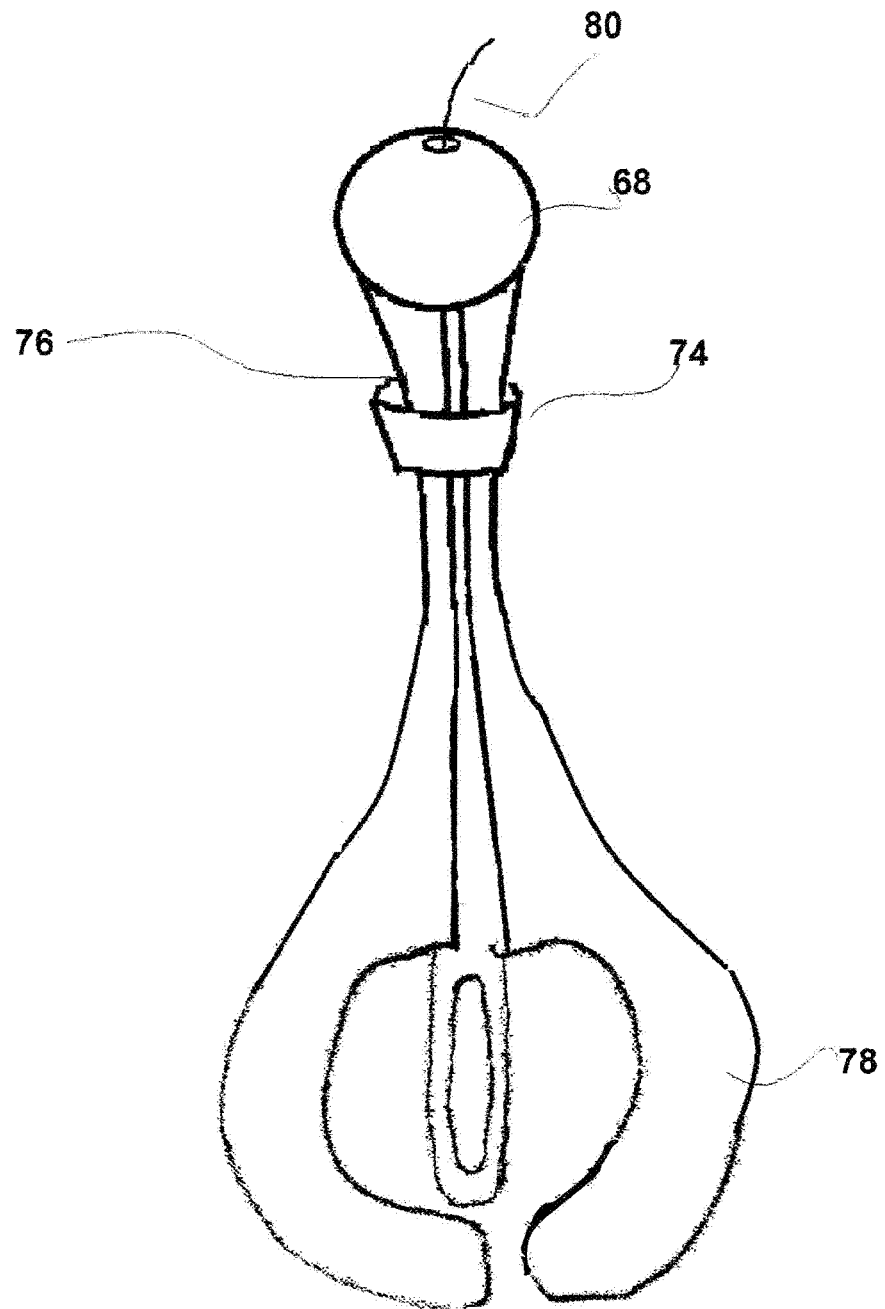
FIG. 5J illustrates a mechanism for using a tensioning chord.
Figure 9:
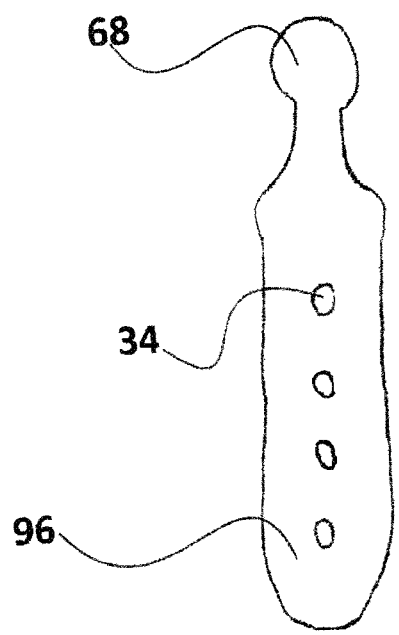
FIG. 9 illustrates a flat paddle tissue holder.

In FIG. 5J (78), as the cord is tightened collar is pulled upward on arms the wedge design of the collar and arm (FIG. 5J (78)) force the jaws to close releasing the tension then relaxes the jaws and allows for repositioning and insertion of another type accessory. Accessories are attached by inserting ball end i.e.: FIG. 9 (68) into locking connector (FIG. 5D) collar (FIG. 5D (74)) is pushed down to lock jaw therefore holding the accessory in a secure position. A mechanism for using a tensioning chord may also be used to tighten the locking jaw (FIG. 5J).

The end connector accessory may be pre-assembled and passed through the trocar or assembled within the patient and attached to octopus arm (FIG. 5) embodies an assembled arm If desired, multiple end sockets FIG. 5D may be added to form extensions and can be attached to each other and individually adjusted to form custom individual positions, shown in FIG. 5E FIG. 5E. is another embodiment made by connecting end clamps in multiple succession by inserting ball FIG. 5D (68) into clamp (FIG. 5D (78)) creating multiple end instrument adjustments connected or fastened to each other to extend or provide additional maneuverability. Collar (FIG. 5D (74)) is a sliding collar to close and lock jaws (FIG. 5D (78)) friction material (FIG. 5D (72)) is added to the Jaws (FIG. 5D (78)) to increase the holding capability. FIG. 5F embodies a completed octopus arm with T connector and end clamp FIG. 5G embodies a completed table with octopus arm assembled.

FIG. 5H embodies a magnet connection (FIG. 5A (190)), may be incorporated in place of the T connector the magnet made of a ferrous material is attached to the Laparoscopic work table using the force of the magnet.

The ability to quickly detach the arm allows the octopus arm with magnet to be used to retrieve sutures dropped into inaccessible locations.

FIG. 6 embodies a method of tightening the tension chord with a small flat or round thumb screw. FIG. 6 (82) is a friction screw when tightened the screw locks in place. When rotated the cord (FIG. 6 (80)) is drawn around reel (FIG. 6 (82)) and creates tension on the Cord (FIG. 6 (80)) Thereby tightening connecting joints.

FIG. 6A embodies FIG. 6 with connecting ball and socket (octopus arm).

Figure 6B:
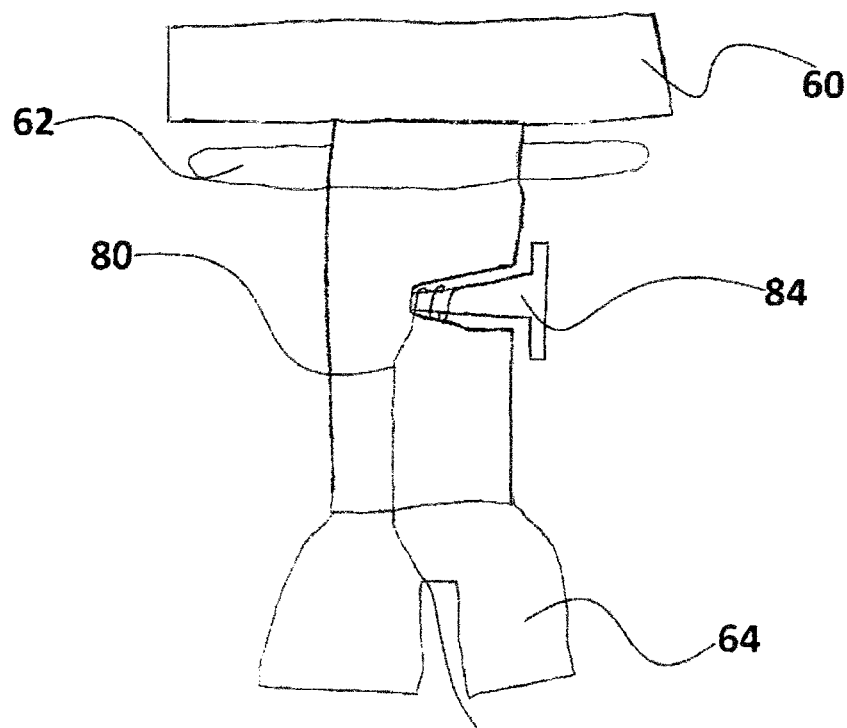
FIG. 6B illustrates tightening a tensioning cord with a screw.

FIG. 6B embodies another method of creating tension on the tightening chord where thumb screw (FIG. 6B (84)) is screwed into the body therefore shortening the chord and creating tension.

Figure 6C:
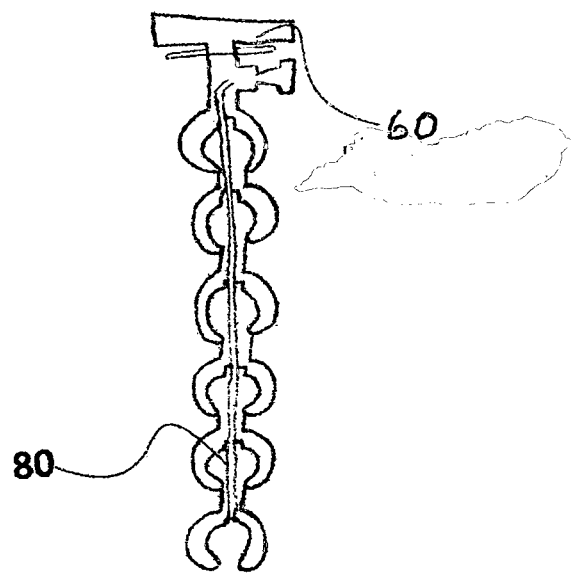
FIG. 6C further illustrates tightening a tensioning cord with a screw.

FIG. 6C embodies another view of completed assembly of the octopus arm

Figure 6D:
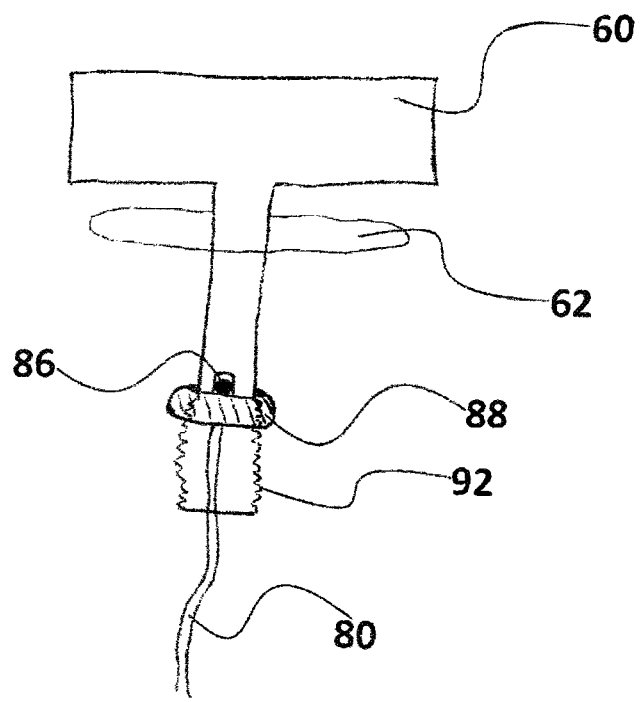
FIG. 6D illustrates a tensioning cord tethered to a pin.

FIG. 6D embodies an additional method of tightening the tensioning cord. The tensioning cord (FIG. 6D (80)) is tethered to pin (FIG. 6D (86)) Pin (86) is in a slot in the T connector with a threaded body. As nut (FIG. 6D (88)) is turned the chord is tightened and therefore locks connectors together.

Figure 7:
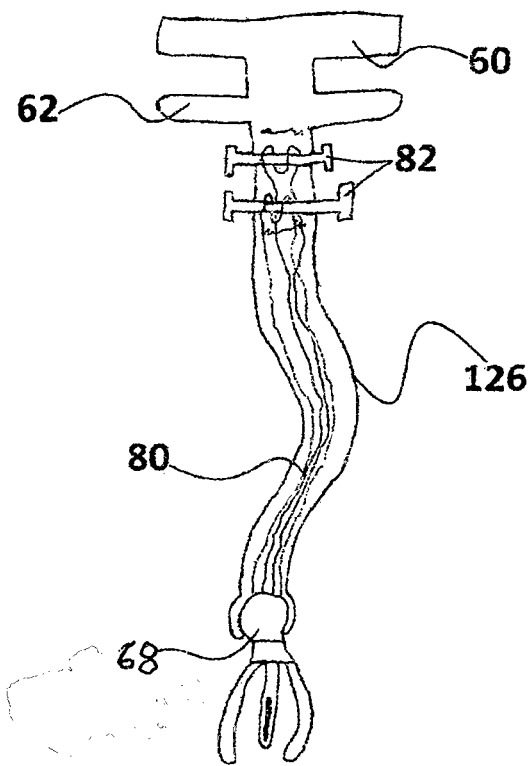
FIG. 7 illustrates the use of multiple cords to steer and lock connectors in different positions.

FIG. 7 embodies multiple cords FIG. 7 (80) to steer and lock connectors in different positions. Each cord is tethered to a different location along the tube wall, or octopus, to individually control the shape or curvature of the arm as screws (FIG. 7 (82)) are adjusted the arm will move in a specific direction depending on the location of the tethered cord. The cords are wound in a capstan method whereas when screw (FIG. 7 (82)) is rotated one side of the cord becomes lose and the other side tightens.

FIG. 8 through FIG. 19 embody different accessory devices used to position and hold tissue and instruments.

Figure 8:
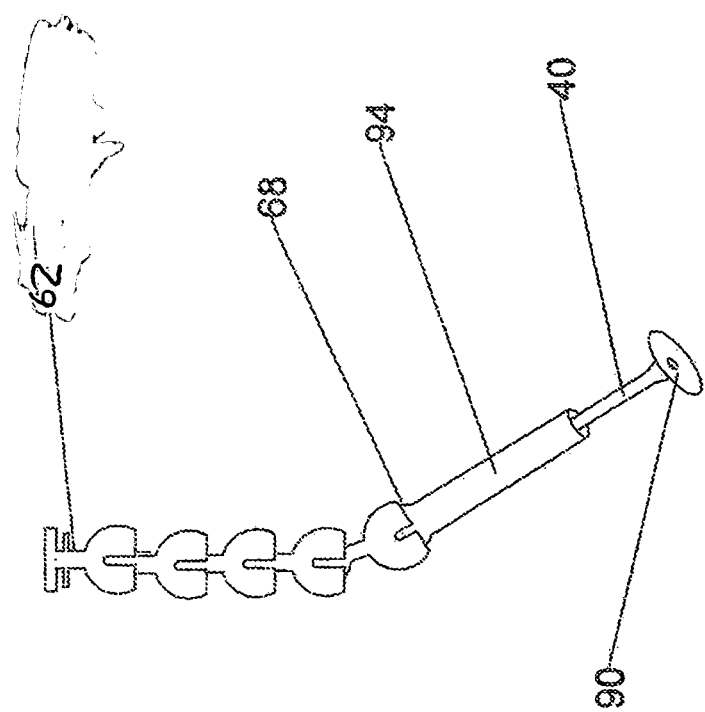
FIG. 8 illustrates an accessory device used to position and hold tissue and instruments.

FIG. 8 embodies a suction manipulator where suction cup (FIG. 8 (90)) and tube (FIG. 8 (40)) is brought in through the suction tube casing (FIG. 8 (94)) to create a suction bond to lift or secure smooth bodied tissues.

FIG. 9 embodies a flat paddle tissue holder. The locking connector (FIG. 5D) is secured on ball connector (FIG. 9 (68)) of paddle (FIG. 9 (96)). The paddle offers holes (FIG. 9 (34)) for additional suture stabilizers.

Figure 10:
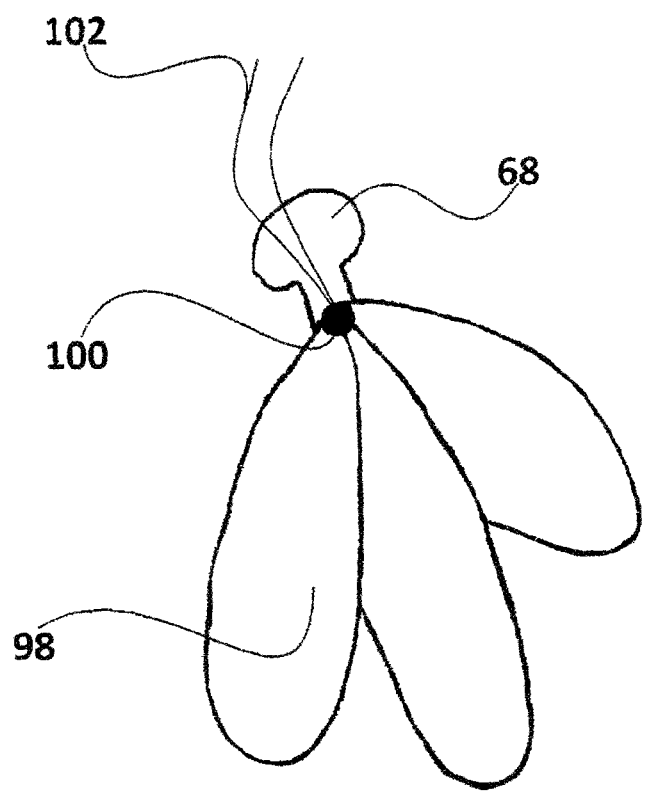
FIG. 10 illustrates a fan retractor.
Figure 10A:
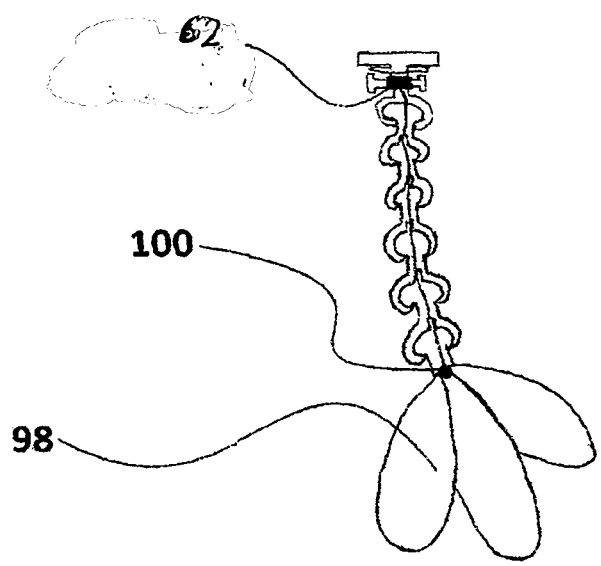
FIG. 10A illustrates a fan accessory attached to an octopus arm.

FIG. 10 is a fan retractor where the paddles 98 hinged on joint (100 are manually expanded using an actuator cord (102 to create a larger surface area. FIG. 10A embodies fan accessory attached to octopus arm.

Figure 12:
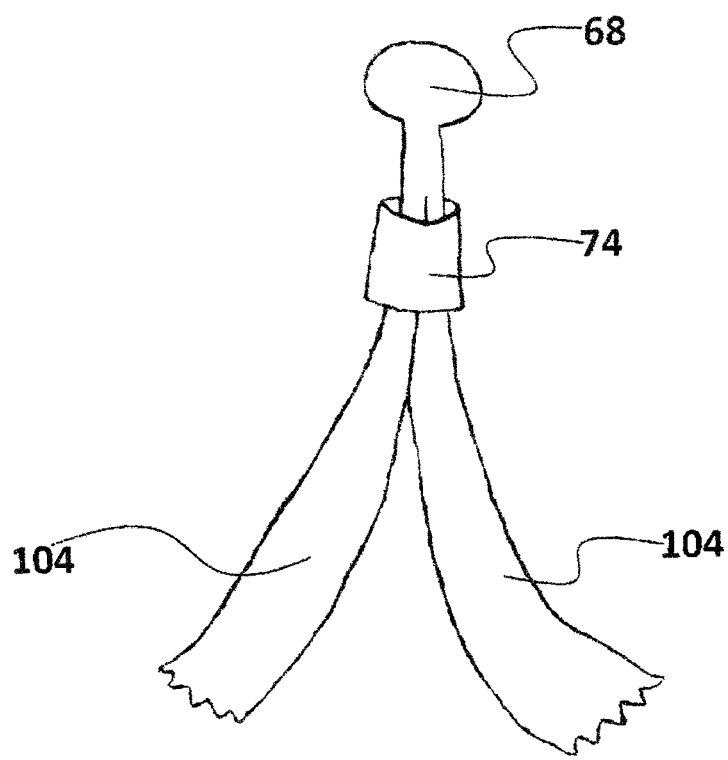
FIG. 12 illustrates a tissue spreader where there is no offset to the spreader legs.
Figure 13:
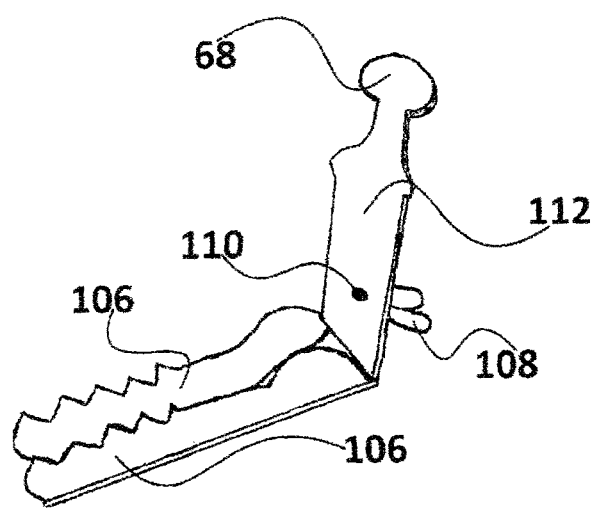
FIG. 13 illustrates an angled clip for grabbing tissue.

FIG. 11 is a tissue spreader device for holding open incisions. The accessory is deployed with collar (FIG. 11 (74)) in the forward or closed position. Once in place the collar is slid back allowing spreader arms (FIG. 11(104)) to open spreading the tissue for access. The device is semi-flexible and at 90 degrees to offset an entry point into the incision FIG. 12 is the identical device as FIG. 11 with the exception that there is no offset to the spreader legs FIG. 13 is angled clip for grabbing tissue. The clip is opened by compressing tabs (FIG. 13 (108)). Hinge joint (FIG. 13 (110)) allows upper jaw (FIG. 13 (106)) and lower jaw (FIG. 13 (106)) to open and close. An internal spring will keep the upper and lower jaws closed until released.

Figure 14:
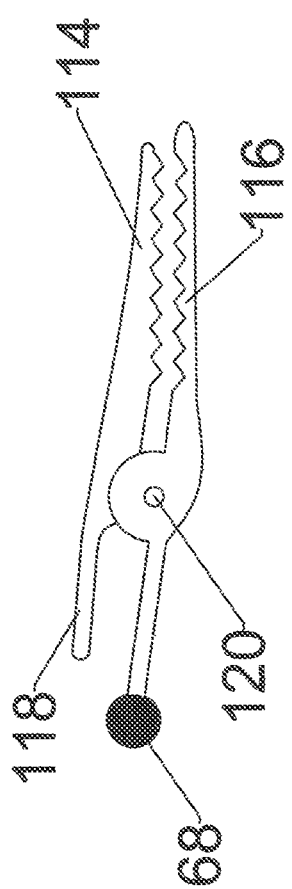
FIG. 14 illustrates another embodiment of a tissue clamp.

FIG. 14 is another embodiment of a tissue clamp. Depressing upper wing (FIG. 14 (118)) opens upper jaw (FIG. 14 (114)) releasing closes jaw to hold tissue between upper Jaw (FIG. 14 (114)) and lower Jaw (FIG. 14 (116)) An internal spring will keep Jaws closed FIG. 15 embodies a balloon dilator to be inflated and expanded to raise or reposition organs or tissues. Air is passed through a tube (FIG. 15 (94)) to inflate balloon (FIG. 15 (124)).

Figure 15:
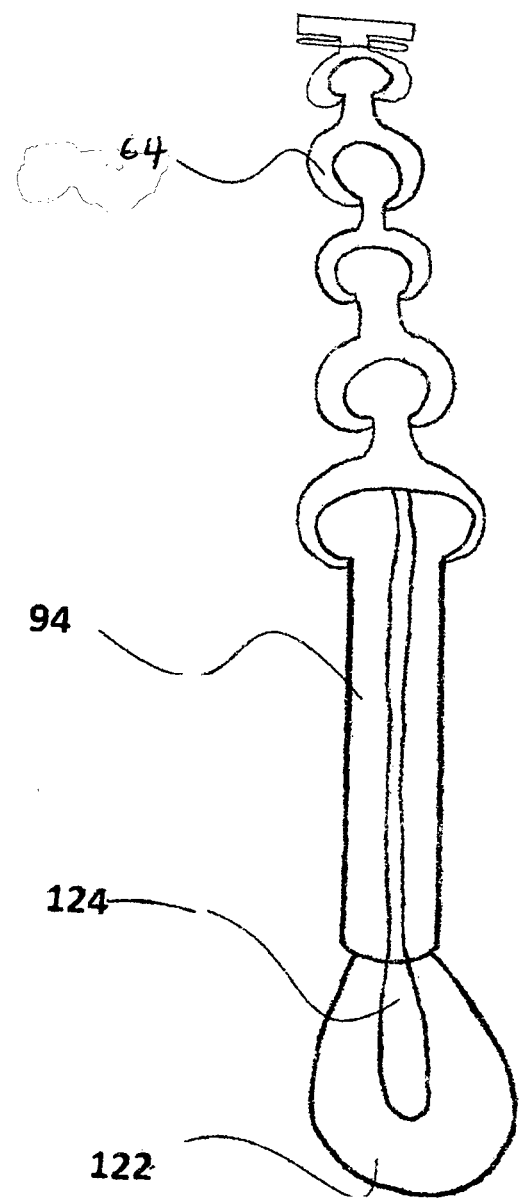
FIG. 15 illustrates a balloon dilator which can be expanded to raise or reposition organs or tissues.

Protective cover may be used (FIG. 15 (122)) as a safety to prevent rupture. An extension tube FIG. 15 (94) is used to extend the reach of the dilator.

Figure 16:
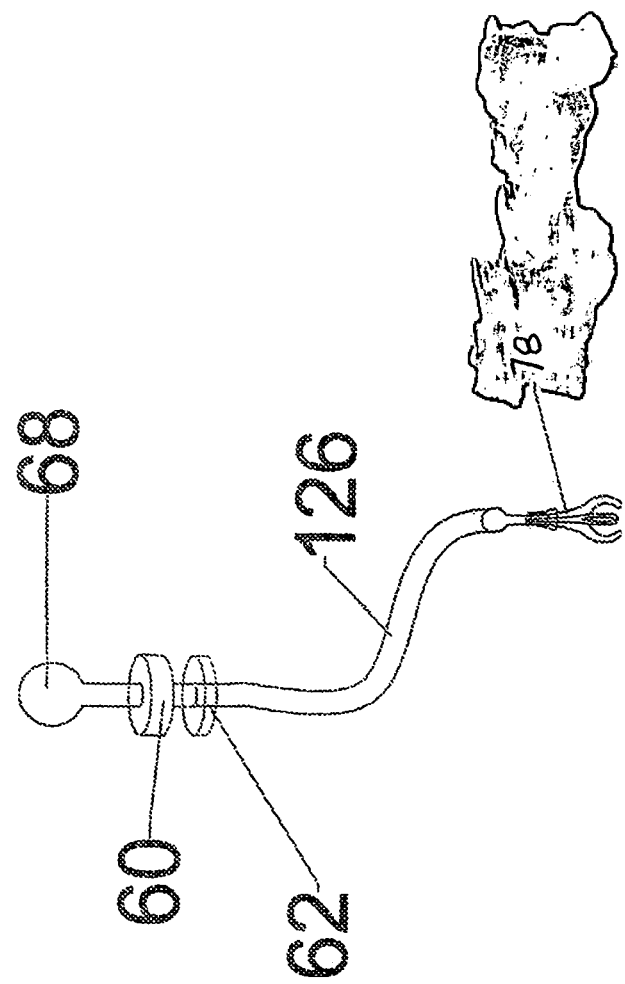
FIG. 16 illustrates a malleable wire for attachment to a base table and that can be shaped to conform to a desired configuration.

FIG. 16 is a malleable wire that can be attached directly to the base table and shaped to conform to desired configuration, A locking clamp (FIG. 5D) can be attached to the bottom of the malleable accessory, to attach other accessories. This can be attached either directly to the base plate or as an extension of the octopus arm. Using locking end clamp (FIG. 5D) on ball (FIG. 16 (68)) FIG. 16 (60) is the locking T and stabilizer plate (FIG. 16 (62)).

Figure 17:
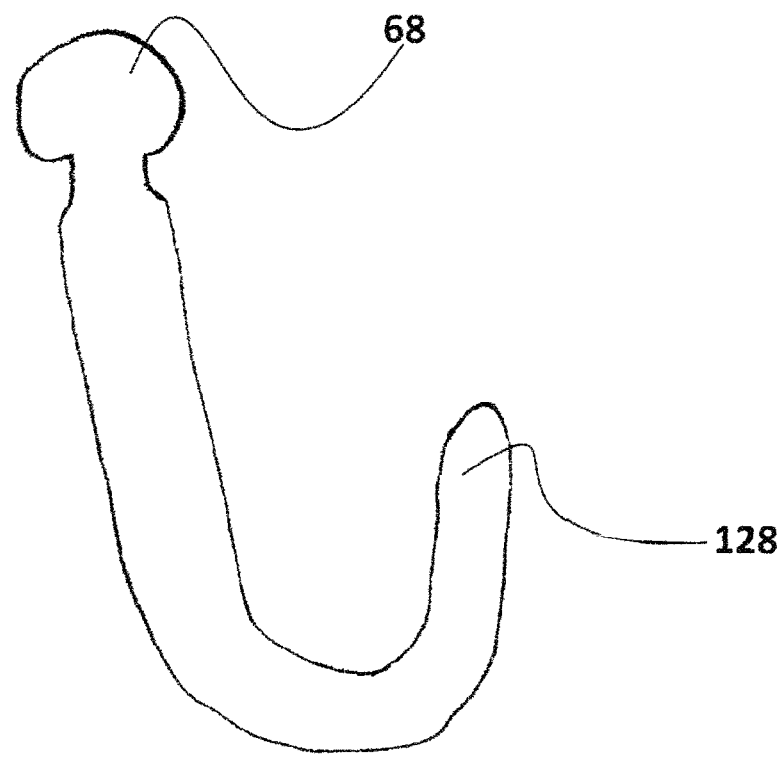
FIG. 17 illustrates a hook retractor for capturing and positioning tissue, veins, arteries or other vessel type structures.

FIG. 17 is a simple hook (FIG. 17 (128)) retractor to capture and position tissue, veins, arteries or other vessel type structures.

Figure 18:
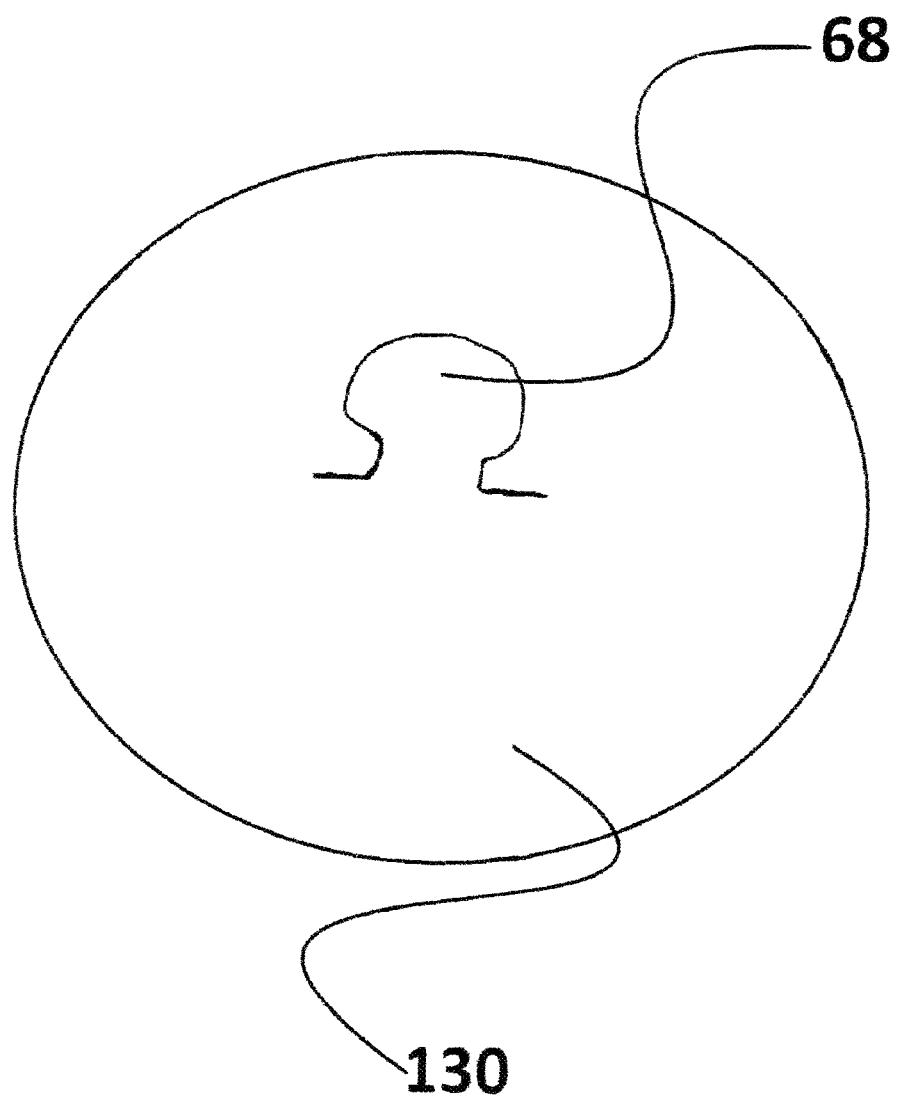
FIG. 18 illustrates is a flexible flat plate that can be rolled up and inserted into a trocar.
Figure 18A:
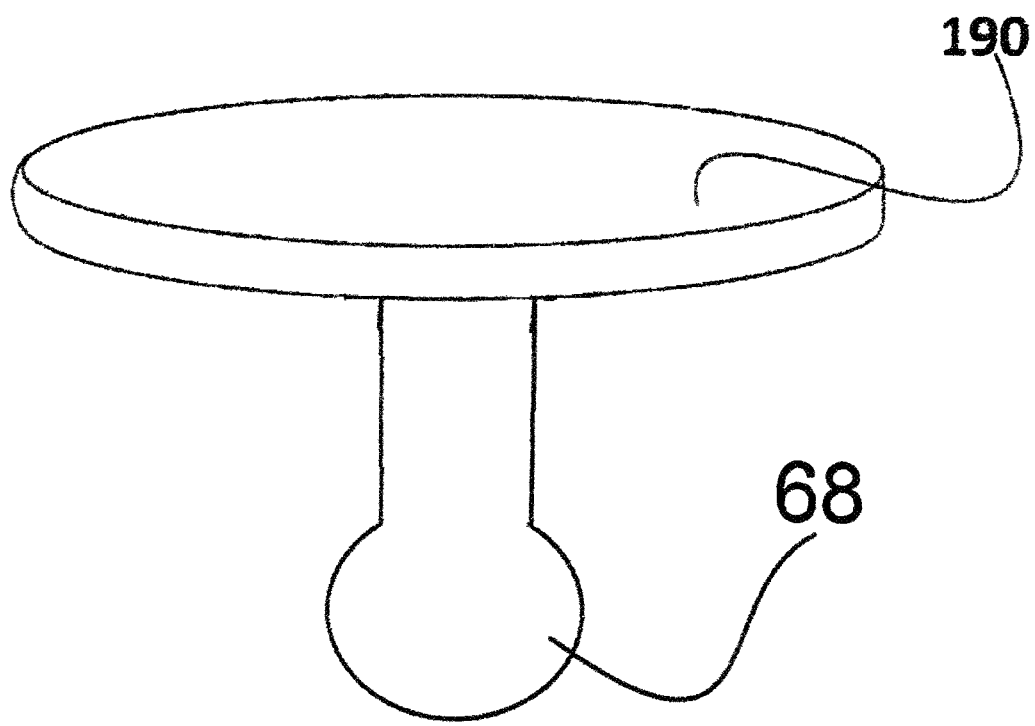
FIG. 18A illustrates a magnetic attachment attached to a ball connector.

FIG. 18 is a flexible flat plate (FIG. 18 (130)) that can be rolled up and inserted into a trocar then attached to the octopus's arm to push tissue into desired position FIG. 18A embodies a magnetic attachment where magnetic surface (FIG. 18A (190)) is attached to a ball connector (FIG. 18A (68)).

Figure 18B:
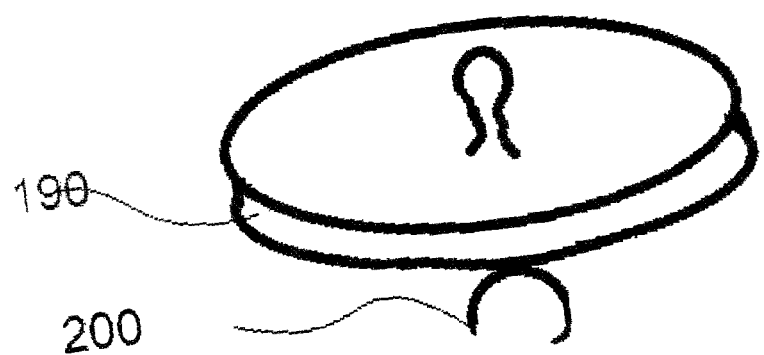
FIG. 18B illustrates a flat accessory with an example of a suture attracted to magnet.

FIG. 18B embodies a magnetic material (FIG. 18B (190)) embedded in flat accessory with an example of a suture (FIG. 18B (200)) attracted to magnet. This device may also be detached to retrieve sutures lost or recovered from difficult to reach locations.

Figure 19:
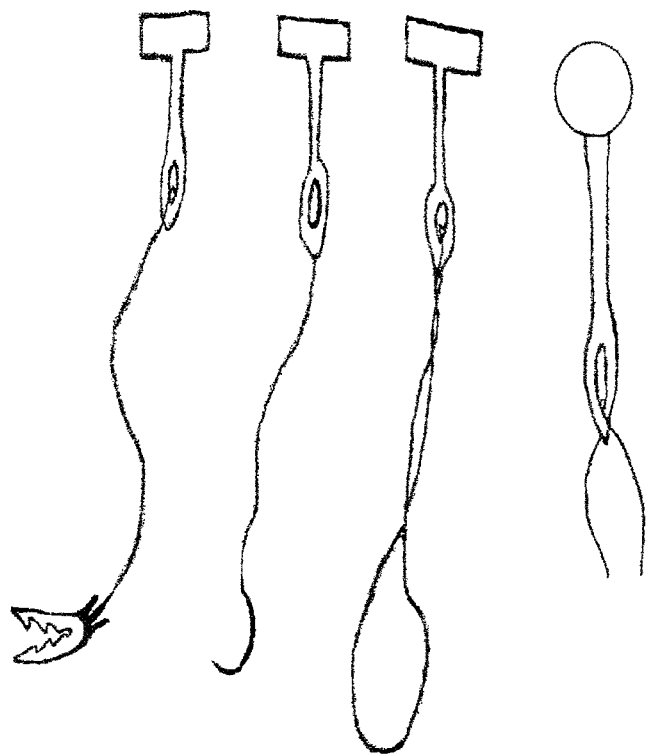
FIG. 19 illustrates suture attachments that can be used to directly attach to the laparoscopic table or end ball connector.

FIG. 19 embodies various suture attachments that can be used to directly attach to the laparoscopic table or end ball connector.

Figure 19A:
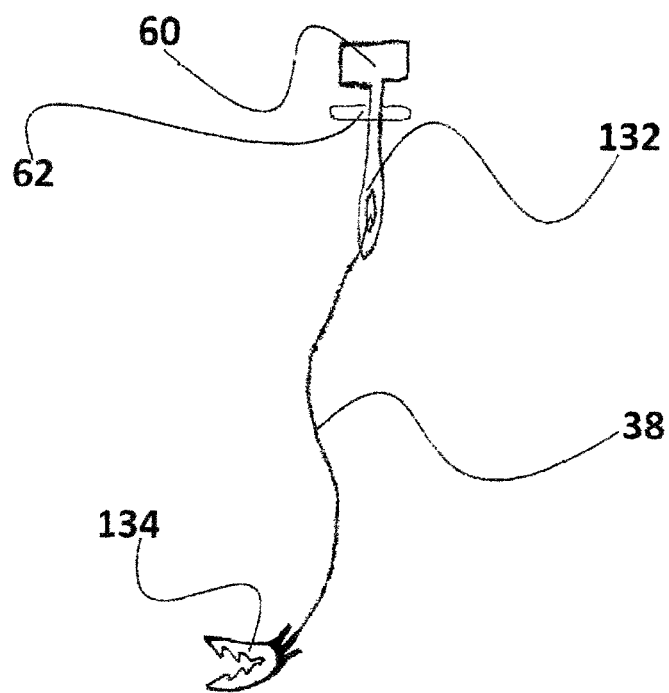
FIG. 19A illustrates a connector with an eyelet to secure a suture tied to a clamp.

FIG. 19A embodies a connector with an eyelet FIG. 19A (132) to secure a suture tied to a clamp FIG. 19A (134)

Figure 19B:
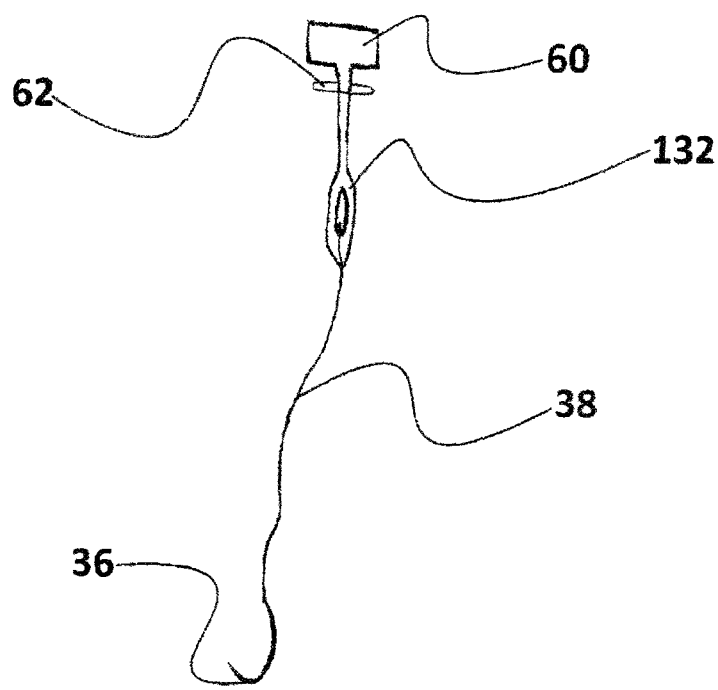
FIG. 19B illustrates a connector with an eyelet to secure a suture tied to a clamp.

FIG. 19B embodies a suture holder with Suture (FIG. 19B (36)) attached to Suture (FIG. 19B (38))

Figure 19C:
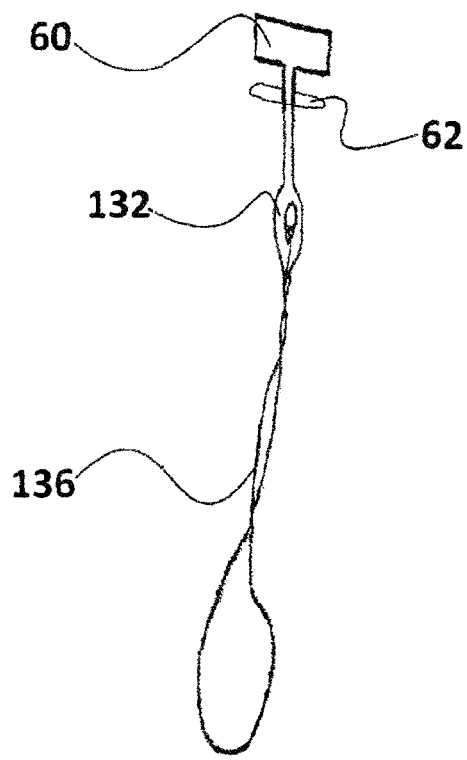
FIG. 19C illustrates a T connector used to hold a vessel loop.
Figure 19D:
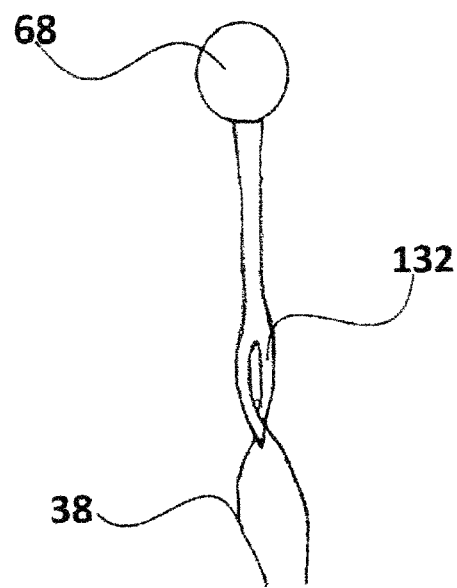
FIG. 19D illustrates a suture holder which can be attached to an end ball connector.

FIG. 19C embodies T connector used to hold vessel loop (FIG. 19C (136)) FIG. 19D embodies a suture holder which can be attached to end ball connector (FIG. 19D (68)).

Figure 20:
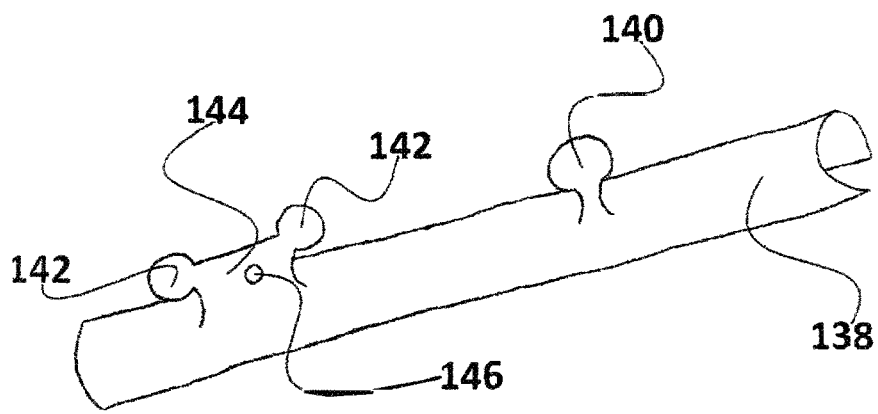
FIG. 20 illustrates an accessory clip to be used with selected instruments.

FIG. 20 embodies an accessory clip to be used with selected instruments with both anvil and ball on it. This clip will help the maneuverability of an instrument by using any of the three balls (FIGS. 20 (140)) and (142) in any desired position and permit both track ball and ridged probe or instrument positioning.

Figure 21:
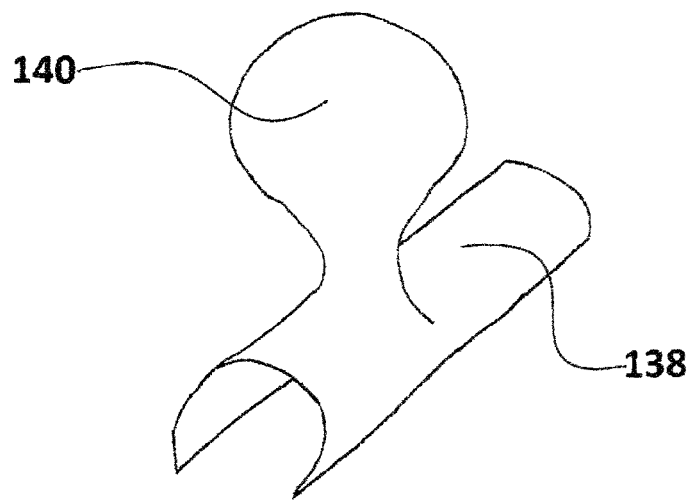
FIG. 21 is an isometric view illustrating a single ball clip.

FIG. 21 is a single ball only clip, this is designed to be used as a "trailer ball" so attached probe can be maneuvered without the control wires on the probe interfering with movement.

FIG. 21 is the single ball only clip, isometric view

Figure 21A:
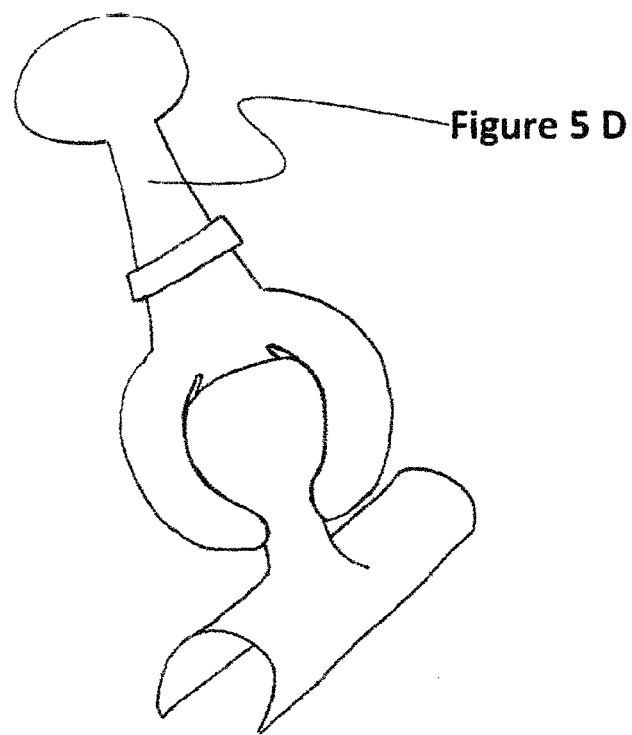
FIG. 21A illustrates a single ball clip designed to be used as a "trailer ball".

FIG. 21A is single ball clip with locking end clamp, (FIG. 5D) attached.

Figure 22:
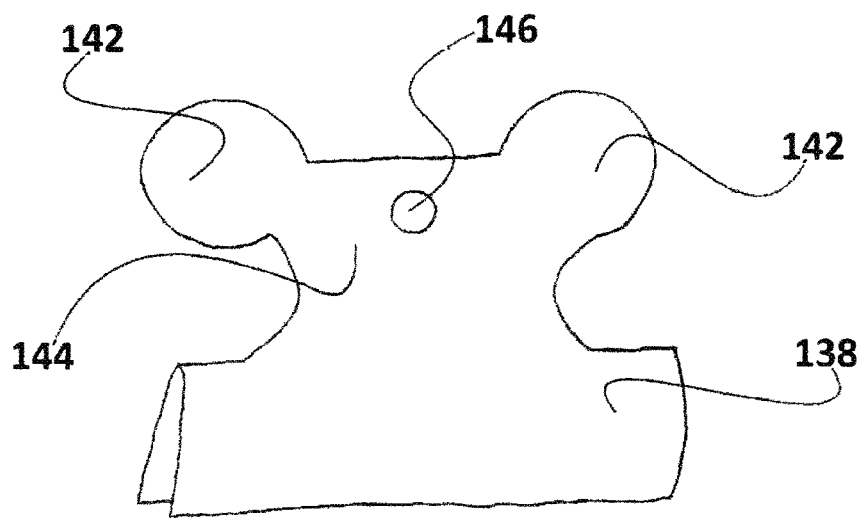
FIG. 22 illustrates a single anvil double ball attachment with balls at each end.

FIG. 22 embodies a single anvil double ball with balls at each end (FIG. 22 (142)) of anvil body (FIG. 22 (144)) device clip (FIG. 22 (138)) is snapped on desired device. A safety suture hole (FIG. 22 (146)) is used for securing or tagging the clip in the remote event it becomes detached.

Figure 23:
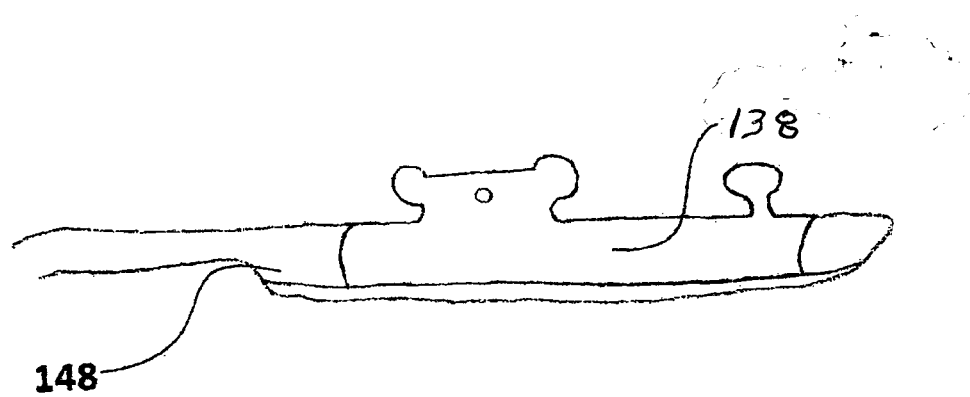
FIG. 23 illustrates a clip on an intraoperative ultrasound probe designed to accept clip.

FIG. 23 embodies application of clip (FIG. 20) on an intraoperative ultrasound probe designed to accept clip (FIG. 20). Two types of protrusions allow for multiple instruments to capture device.

Figure 24:
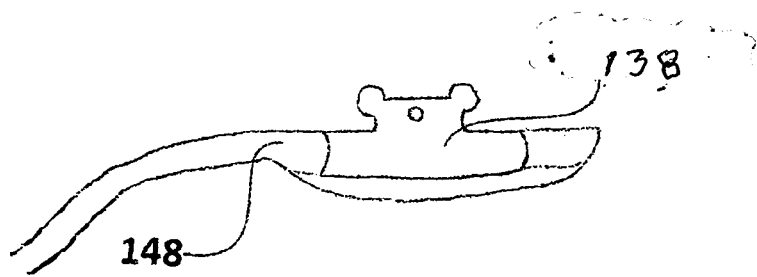
FIG. 24 illustrates an ultrasound probe designed to accept a clip, and for use with laparoscopic worktable.

FIG. 24 embodies another embodiment of anvil only clip used on an intraoperative ultrasound probe FIG. 24 embodies an ultrasound probe designed to accept clip (FIG. 22) for use with a laparoscopic worktable.

Figure 25:
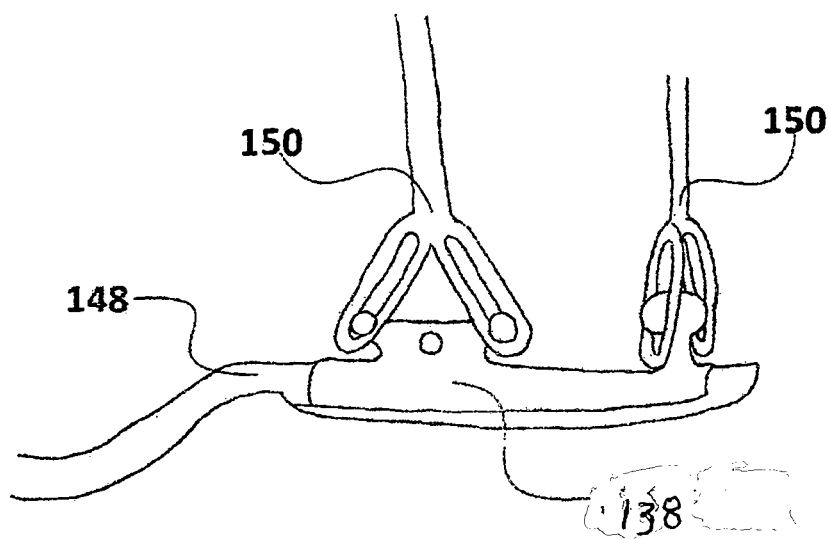
FIG. 25 illustrates a clip attached to an ultrasound probe that can be maneuvered using robotic or laparoscopic graspers.

FIG. 25 embodies a clip attached to an ultrasound probe. FIG. 25 (148) can be maneuvered using robotic or laparoscopic graspers (FIG. 25 (150)).

FIG. 25, FIG. 26, FIG. 27, and FIG. 28 show different methods of capturing clip (FIG. 20).

Figure 26:
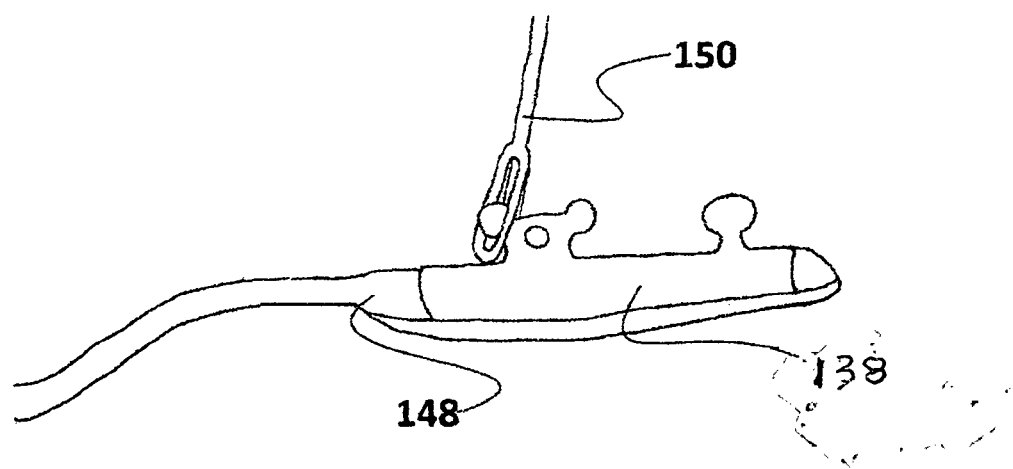
FIG. 26 illustrates a clip attached to an ultrasound probe with a grabber attachment attached to the anvil thereof, by the fork at the end of the grabber.

FIG. 26 embodies the anvil clip attached to an ultrasound probe and the grabber attachment attached to the anvil by the fork at the end of the grabber.

FIG. 25 embodies the clip attached to an ultrasound probe with two graspers attached to the clip at both anvil and ball only. One grasper grabs the anvil from the top and locks into position by the balls on each end. The second grasper shown is grabbing the single ball by the top and is secured into place.

FIG. 26 embodies single grasper capturing one ball on anvil

Figure 27:
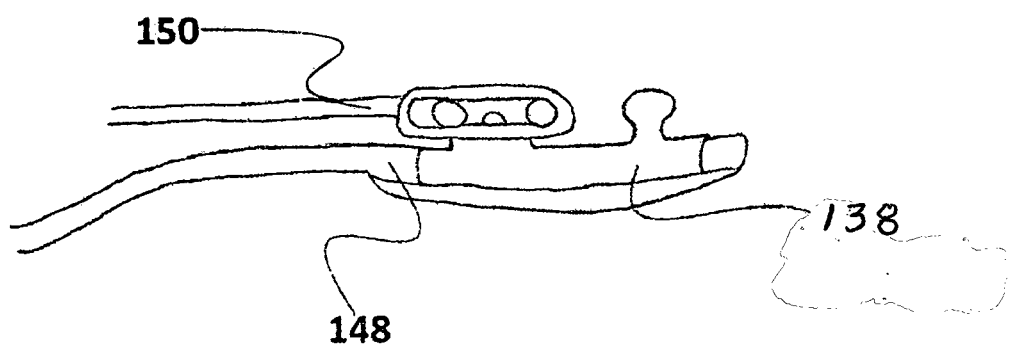
FIG. 27 illustrates a clip, attached to an ultrasound probe, and grasped from an end to provide firm end control.

FIG. 27 embodies how the clip is grasped from end to provide a firm end control of clip attached to an ultrasound probe.

Figure 28:
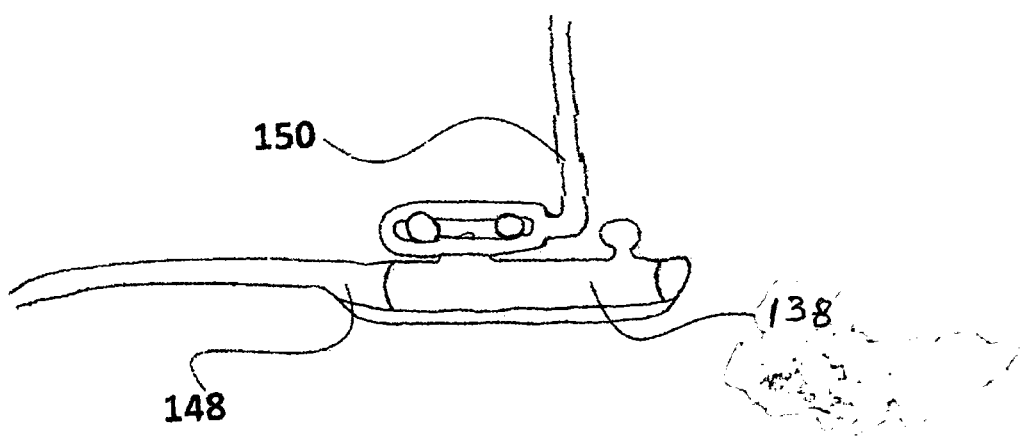
FIG. 28 illustrates another method for grasping a clip attached to an ultrasound probe.

FIG. 28 embodies another method of grasping clip attached to ultrasound probe.

FIG. 28 embodies the clip attached to a probe with the grasper vertically grasping both balls on the anvil clip for a more stable maneuverability of probe.

Figure 29:
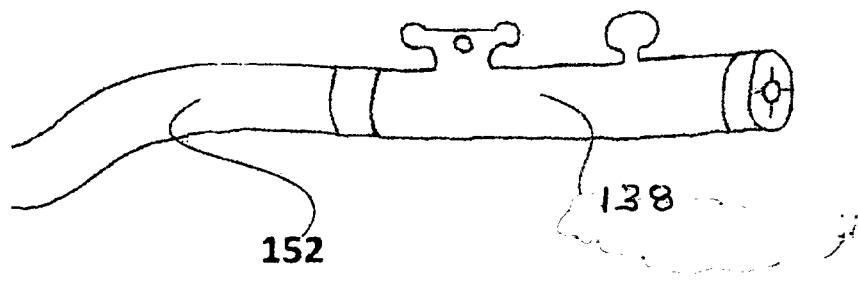
FIG. 29 illustrates a clip attached to intraoperative camera.

FIG. 29 embodies clip attached to intraoperative camera. (FIG. 29 (152))

Figure 30:
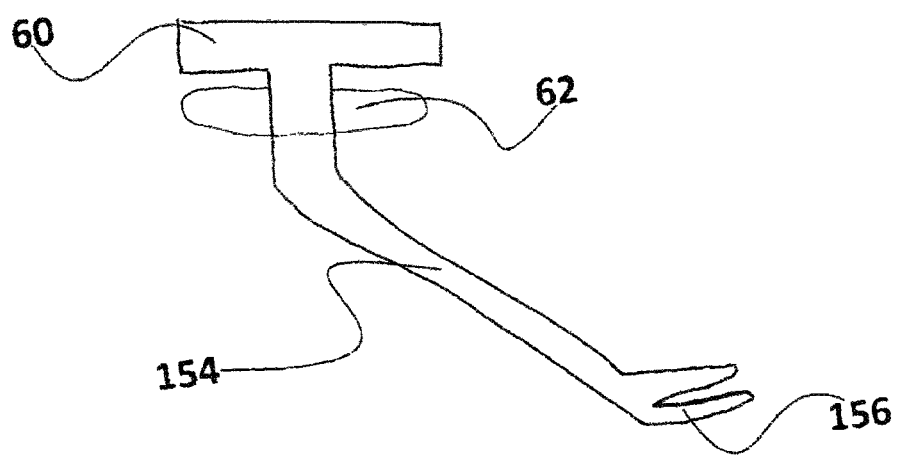
FIG. 30 illustrates an accessory handle attached to single anvil clip.

FIG. 30 embodies an accessory that may be attached to the clip for use in a fixed or handheld operation.

Figure 30A:
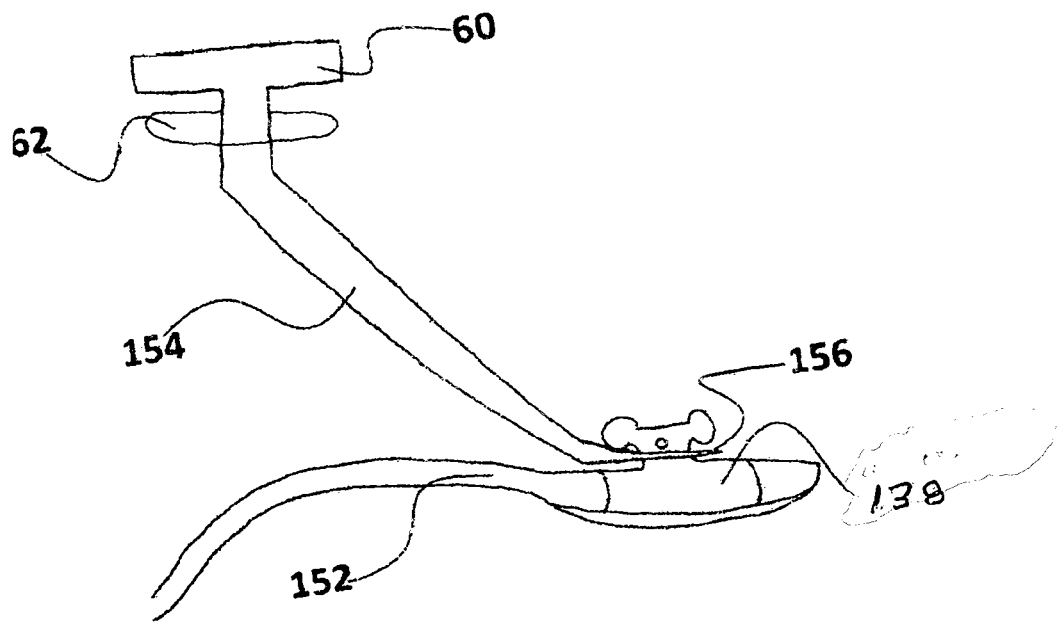
FIG. 30A illustrates an accessory handle attached to single anvil clip, with intraoperative ultrasound, attached for laparoscopic table operations.

FIG. 30A embodies accessory handle attached to single anvil clip (FIG. 22) with intraoperative ultrasound (FIG. 30A (142)) attached for laparoscopic table operations.

Figure 30B:
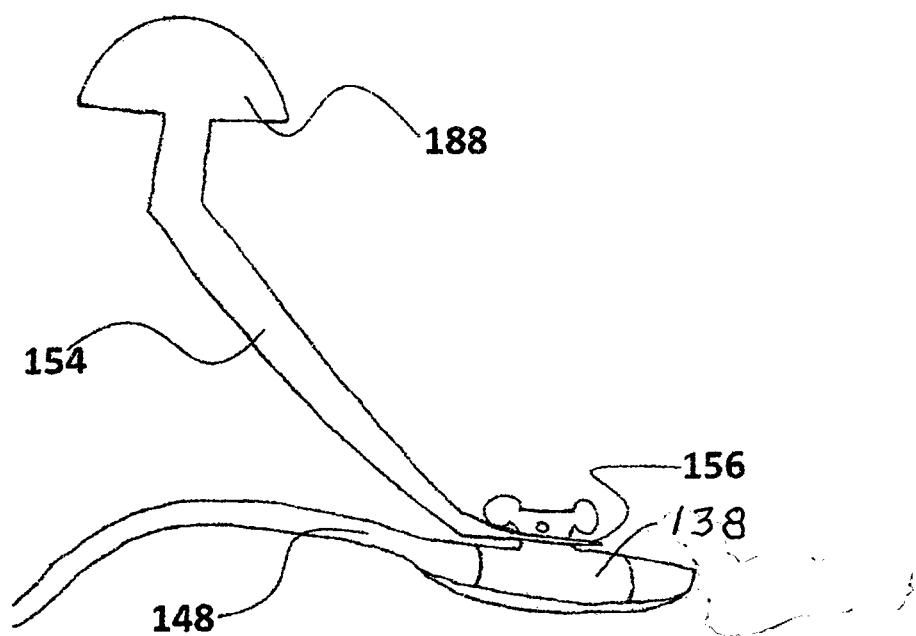
FIG. 30B illustrates a handheld clip with a handle attached to a ridged arm.

FIG. 30A extension arm (FIG. 30A (154)) may be of various lengths or designs with ridged or malleable arms to accommodate easier access of the ultrasound probe FIG. 30B embodies handheld clip with handle (FIG. 30B (188)) attached to a ridged arm (FIG. 30B (154)). V clip (FIG. 30B (156)) is designed to snap on clip (FIG. 30B (154)) and provide for more ridged control of devices attached to clip (FIG. 22).

Figure 31:
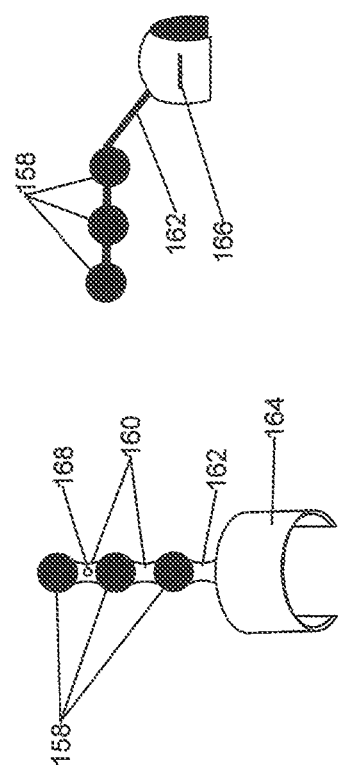
FIG. 31 illustrates is universal clip for attachment to other surgical devices.
Figure 31A:
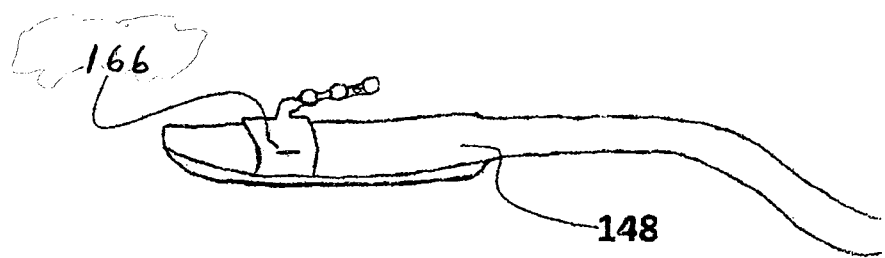
FIG. 31A illustrates a clip for attachment to an ultrasound transducer.

The clips of FIGS. 20, 21 and 22 or of FIG. 31 may also be used over a sterile disposable cover offering less possibility of contamination of surgical equipment FIG. 31 is universal clip to be attached to other surgical devices such as a camera (FIG. 31D) or an ultrasound transducer (FIG. 31A) and can be used with laparoscopic table or captured and manipulated by other surgical instruments.

Figure 31D:
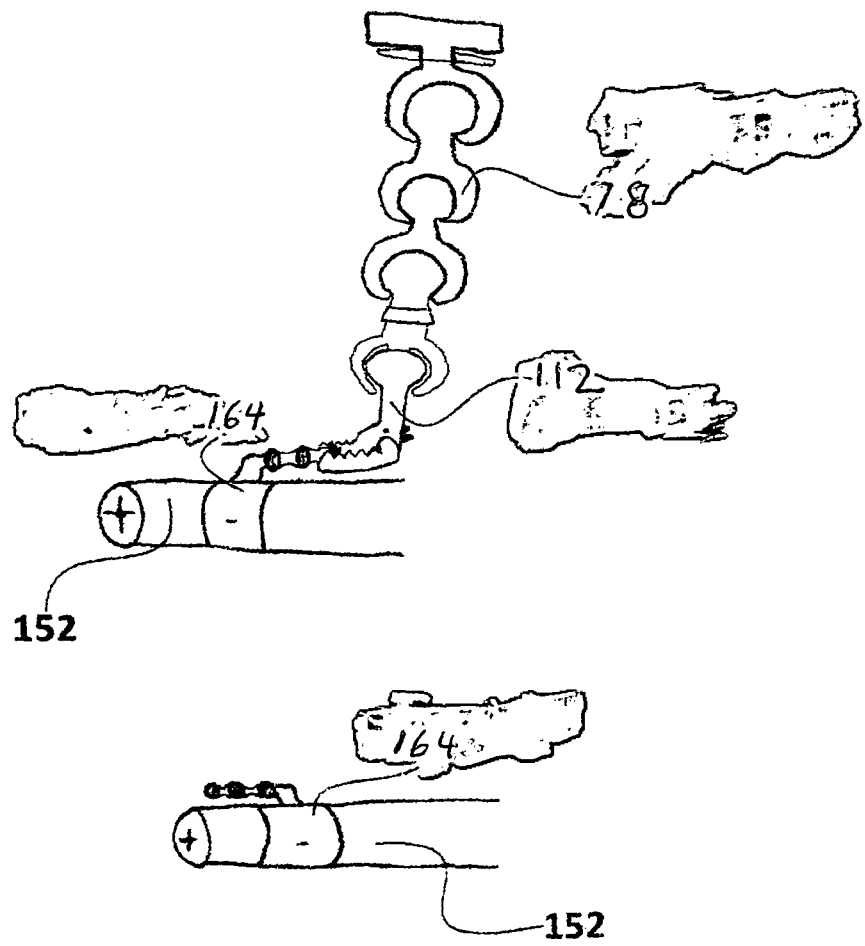
FIG. 31D illustrates a clip to be attached to other surgical devices such as a camera or ultrasound transducer.

Balls on the clip (FIG. 31 (158)) with indents on the spring (FIG. 31 (160)) allow the attached instrument to be captured in various positions. FIG. 31D embodies a camera (FIG. 31D (152) captured by clip using accessory FIG. 13. This may also be attached to an ultrasound (FIG. 31A (148)) or another device.

The clip arm (FIG. 31 (160)) is attached to a spring clamp (FIG. 31 (164) to make the universal clip accessory The material is made from spring steel or other memory material to slide over and secure desired instrument. Balls (FIG. 31 (160)) on the handle or arm (FIG. 31 (160)) are strategically placed to offer various grasping positions. Handle area FIG. 31 (160) provide a gradual relief for extraction from the trocar to avoid damaging Trocar seals. Detents (FIG. 31 (160)) allow additional grasping positions The embodied clips (FIGS. 20, 21 and 22, or FIG. 31) can be reversed for additional positioning options. The clip may also be used with other grasping instruments used in laparoscopic or open procedures. The clips may be made to be reusable or disposable material depending on the requirements of the facility.

FIG. 31B embodies two methods of providing a safety to secure the clip. FIG. 31B (170) is a spring to be wrapped around clip and device while FIG. 31B (172) and (174) are rotating locking collars.

The locking collar (FIG. 31B (172,174)) or other type of locking device is rotated or compressed to lock the clip. This ensures the clip is securely fastened to the device. An expanding spring (FIG. 31B (170)) with memory material may also be used to secure the clip onto the device.

FIG. 32 is an example of the devices used in a procedure.

Figure 33:
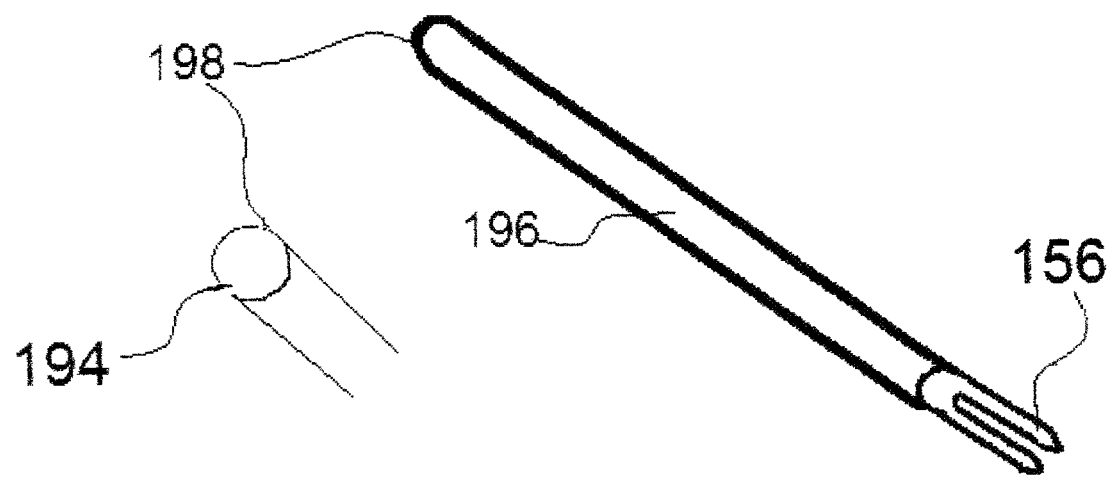
FIG. 33 illustrates a device with a ridged tube and an attached probe or camera that can be inserted through a trocar and manipulated with the ridged tube.

FIG. 33 embodies an accessory device to pass probes through trocar and maintain insufflation It also can be used as a holder for laparoscopic use. 1001701A probe or camera is inserted into the seal end of the tube (FIG. 33 (190)) and pushed past the capture device (156) The probe is then withdrawn ensuring the anvils on the clip, (FIG. 22 (144)) captured and snapped into the capture jaws (FIG. 33 (156)).

The seal (FIG. 33 (194)) limits loss of insufflation. The device attached (probe or camera) can be inserted through a trocar and manipulated by the ridged tube (FIG. 33 (188))

Figure 33A:
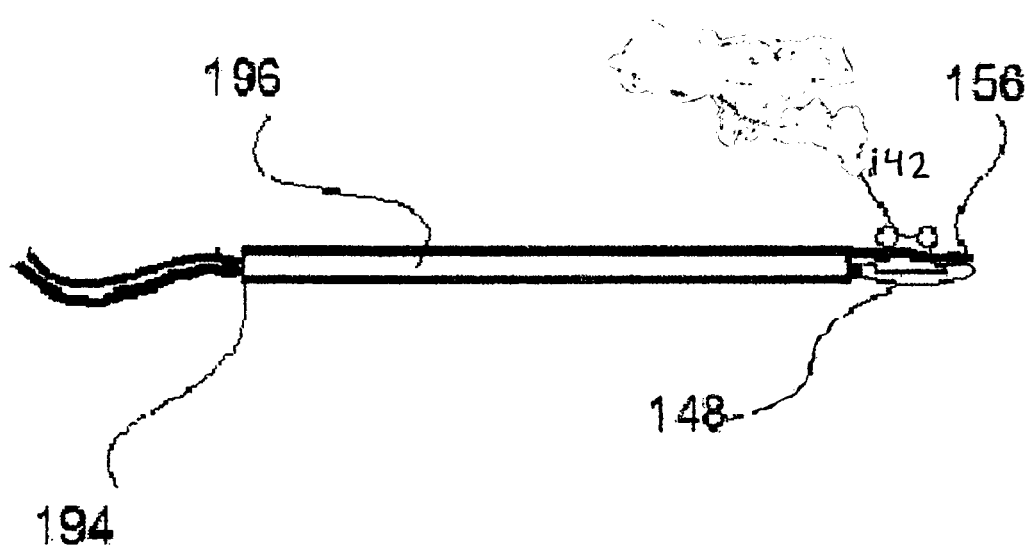
FIG. 33A illustrates an ultrasound probe with an attached clip.

FIG. 33A embodies an ultrasound probe (FIG. 33A with clip (FIG. 22) attached.

The invention claimed is:

1. A surgical table comprising:
a main plate;
a first pivot member attached to said plate;
two stabilizer wings pivotally attached to said main plate at said first pivot member, said stabilizer wings being movable when pivoting between a collapsed configuration wherein the stabilizer wings do not extend from said main plate, and an expanded configuration wherein the stabilizer wings extend from said main plate; and
said surgical table being configured to permit said surgical table to be affixed to an interior surface of a body cavity.

2. The surgical table of claim 1, further comprising:
a second pivot member disposed in a slot in said main plate;
an actuator for each of said stabilizer wings, said actuators being attached to a second pivot point, each actuator being for moving each of said stabilizer wings between said collapsed configuration and said expanded configuration, in accordance with a position of said second pivot member in said slot.

3. The surgical table of claim 1, wherein a second pivot point for said stabilizer wings is configured as a grommet, further comprising a deployment cord affixed to said second pivot point for causing movement of said second pivot point along a slot in said main plate.

4. The surgical table of claim 1, wherein a first pivot point for said stabilizer wings is configured as a grommet through which a suture is placed.

5. The surgical table of claim 1, further comprising a second pivot point for said stabilizer wings; and a deployment cord for causing movement of said second pivot point along a slot in said main plate.

6. The surgical table of claim 1, further comprising a suture extending through an abdominal wall of a patient to secure the surgical table in place within an abdomen of a patient.

7. The surgical table of claim 6, in combination with a tensioning device for placement external to said abdominal wall to cause tension in said suture.

8. The surgical table of claim 1, further comprising a cushion on the surgical table to protect surfaces from abrasion by the surgical table.

9. The surgical table of claim 1, in combination with a suction tube passed through a first pivot point.

10. The surgical table of claim 1, in combination with an accessory arm, the accessory arm having a connector for locking the accessory arm to the surgical table.

11. The surgical table of claim 9, wherein the connector is a T-lock, which has a T member that fits into a slot in the surgical table, the connector being rotated by 90 degrees to lock the connector to the surgical table.

12. The surgical table of claim 11, further comprising a foam member disposed between the T member and the surgical table for assisting in keeping the connector in a fixed position with respect to the surgical table.

13. The surgical table of claim 10, wherein the accessory arm is made of a flexible, malleable material.

14. The surgical table of claim 10, wherein the accessory arm comprises a series of ball and socket knuckles.

15. The surgical table of claim 14, wherein the sockets of the ball and socket knuckles are coated with a high friction coating to assure that the accessory arm remains rigid unless acted up by sufficient for to overcome friction of the high friction coating.

16. The surgical table of claim 14, wherein the sockets of the ball and socket knuckles have a series of slits, further comprising a locking cord around the socket to compress the slits and to thereby lock the ball and socket in a desired relative orientation.

17. The surgical table of claim 10, wherein the accessory arm further comprises a locking connector for holding an object.

18. The surgical table of claim 17, wherein the locking connector has arms for gripping the object, and a collar for causing the arms to close on the object.

19. The surgical table of claim 10, wherein the connector is a magnetic connector, the magnetic connector holding the accessory arm to the surgical table.

20. The surgical table of claim 10, wherein the accessory arm further comprises a cord along a length of the accessory arm, and a cord tensioner for manipulating the cord to control movement of the accessory arm.

21. The surgical table of claim 20, wherein the cord tensioner comprises a screw around which the cord tensioner is wound.

22. The surgical table of claim 20, wherein the accessory arm has a threaded portion, with a slot extending in a direction along a portion of length of the threaded portion, and the cord tensioner comprises:
a pin to which the cord is tethered, the pin being disposed in the slot, and
a nut engaging the threaded portion so that when the nut is rotated and travels along the threaded portion, the nut engages the pin to move along the slot to provide tension in the cord.

23. The surgical table of claim 10, wherein the accessory arm further comprises a suction manipulator having a suction cup and suction tube, to create a suction bond to lift or secure smooth bodied tissues.

24. The surgical table of claim 10, wherein the accessory arm further comprises a surgical tool selected from the group consisting of a flat paddle tissue holder, a fan retractor, a tissue spreader, and angled clip, a tissue clamp, a balloon dilator, a malleable wire, a hook, an unrolled flexible plate, a detachable magnetic member for retrieving suture needles, a suture holder; an eyelet, and a vessel loop.

25. The surgical table of claim 10, wherein the accessory arm further comprises an accessory clip having extending therefrom at least one of a ball and an anvil.

26. The surgical table of claim 25, further comprising an accessory clip having extending therefrom at least one of a ball and an anvil, the accessory clip for receiving an intraoperative instrument.

27. The surgical table of claim 25, further comprising an accessory clip having extending therefrom at least one of a ball and an anvil, the accessory clip being for receiving an ultrasonic probe, the accessory clip being held by a grasping device associated with said table.

28. The surgical table of claim 25, further comprising an accessory clip having extending therefrom at least one of a ball and an anvil, the accessory clip being for receiving an intraoperative camera, the accessory clip being held by a grasping device associated with said surgical table.

29. The surgical table of claim 1, further comprising a grasping device associated with said surgical table, said grasping device being for grasping an accessory clip that receives a surgical instrument.

30. The surgical table of claim 1, further comprising a grasping device associated with said surgical table, said grasping device being for grasping an accessory clip that receives an insufflation device.

31. The surgical table of claim 1, in combination with a cushion on an outer wall of a body cavity opposite the surgical table so that the outer wall of the body cavity is positioned between the cushion and the surgical I table when the surgical table is affixed to the interior surface of the body cavity.

32. The surgical table of claim 31, further comprising at least one suture extending through the outer wall of the body cavity to the cushion, the suture securing the surgical table against the interior surface of the body cavity.

* * * * *